(12) United States Patent
Godzik et al.

(10) Patent No.: US 7,504,205 B2
(45) Date of Patent: Mar. 17, 2009

(54) UNCHARACTERIZED ORF3 IN SARS-CORONAVIRUS IS A CYCLIC-AMP-DEPENDENT KINASE AND A TARGET FOR SARS THERAPY

(75) Inventors: Adam Godzik, San Diego, CA (US); Sergey Sikora, San Diego, CA (US)

(73) Assignee: The Burnham Institute, San Diego, CA (US)

( * ) Notice: Subject to any disclaimer, the term of this patent is extended or adjusted under 35 U.S.C. 154(b) by 372 days.

(21) Appl. No.: 11/132,142

(22) Filed: May 17, 2005

(65) Prior Publication Data

US 2005/0276818 A1  Dec. 15, 2005

Related U.S. Application Data

(60) Provisional application No. 60/571,698, filed on May 17, 2004.

(51) Int. Cl.
*C12Q 1/70* (2006.01)
*C12Q 1/48* (2006.01)
*C12Q 1/18* (2006.01)

(52) U.S. Cl. ................................ 435/5; 435/15; 435/32

(58) Field of Classification Search ........................ None
See application file for complete search history.

(56) References Cited

U.S. PATENT DOCUMENTS

| 4,376,110 | A | 3/1983 | David |
| 4,946,778 | A | 8/1990 | Ladner |
| 5,264,563 | A | 11/1993 | Huse |
| 5,625,048 | A | 4/1997 | Tsien |
| 5,777,079 | A | 7/1998 | Tsien |
| 5,804,387 | A | 9/1998 | Cormack |

OTHER PUBLICATIONS

Muegge et al. current Medicinal Chemistry 11:693-707, 2004.*
Lu et al. PNAS 103:12540-12545, 2006.*
Zeng et al. Journal of Molecular Biology 341:271-279, 2004.*
Cartier et al (Journal of Biological Chemistry 278:35211-35219, Sep. 2003).*
Huse, W., et al., Generation of a Large Combinatorial Library of the Immunoglobulin Repertoire in Phage Lambda, Science 1989;246:1275-81.
Huston, J., et al., Protein engineering of antibody binding sites: Recovery of specific activity in an antidigoxin . . ., Proc Natl Acad Sci 1988;85:5879-83.
Kohler, G. and Milstein, C., Continuous Cultures of Fused Cells Secreting Antibody of Predefined Specificity, Nature 1975;256:495-7.
Kozbor, D., and Roder, J., The Production of Monoclonal Antibodies from Human Lymphocytes, Immunology Today 1983;4:72-9.
Ksiazek, T., et al., A Novel Coronavirus Associated with Severe Acute Respiratory Syndrome, N Engl J Med 2003;348:1953-66.
Kuiken, T., et al., Newly discovered coronavirus as the primary cause if severe acute respiratory syndrome, Lancet 2003;362:263-70.
Marra, M., et al., The Genome Sequence of the SARS-Associated coronavirus, Science 2003; 300:1399-1404.
Morrison, S., et al., Chimeric human antibody molecules: Mouse antigen-binding domains with human constant . . . , Natl Acad Sci 1984;81:6851-5.
Myint, S., Human Coronavirus Infections, The Coronaviridae 1995;389-401.
Neuberger, et al., Recombinant antibodies processing novel effector functions, Nature 1984;312:604-8.
Bird, R., et al., Single Chain Antigen Binding Proteins, Science 1988;242:423-6.
Cartier, C., et al., Active cAMP-dependent Protein Kinase Incorporated within Highly Purified HIV-1 Particles is Required for Viral . . . , J Biol Chem 2003;278-35211-9.
Cote, R., et al., Generation of human monoclonal antibodies reactive with cellular antigens, Proc Natl Acad Sci USA 1983;80:2026-2030.
Cubitt, A., et al., Understanding Structure-Function Relationships in the Aequorea victoria Green Fluorescent Protein, Methods in Cell Biology;58:19-30.
Cyranoski, D., and Abbott, A., Virus Detectives Seek Source of SARS in China's Wild Animals, Nature 2003;423:467.
Eichler, J., et al., Peptide, Peptidomimetic, and Organic Synthetic Combinatorial Libraries, Med Res Rev 1995;15:481-496.
Fouchier, R., et al., Koch's postulates fulfilled for SARS virus, Nature 2003;423:240.
Francis, M. et al., Combinatorial Libraries of Transition-metal Complexes, Catalysts and Materials, Curr Opin Chem Biol 1998;2:422-8.
Holmes, K., Coronaviruses, Fields' Virology 2001;1187-1203.
Holmes, K., SARS coronavirus: a new challenge for prevention and therapy, J Clin Inves 2003;111:1605-9.
Peiris, J., et al., Coronavirus as a possible casue of severe acute respiratory syndrome, Lancet 2003;361:1319-25.
Prasher, D., et al., Primary structure of the Aequorea victoria greenfluorescent protein, Gene 1992;111:229-33.
Ruan, Y., et al., Comparative full-length genome sequence analysis of 14 SARS coronavirus isolates and common . . . , Lancet 2003;361:1779-85.

(Continued)

*Primary Examiner*—Mary E Mosher
(74) *Attorney, Agent, or Firm*—Catalyst Law Group APC; David M Kohn

(57) ABSTRACT

The present invention relates to novel methods for identifying antiviral agents which selectively interfere with viral proteins that cause the unique infectivity activity of the SARS-coronavirus in comparison to other non-SARS strains of coronavirus. In particular, the present invention relates to screening assays that identify agents which selectively inhibit c

OTHER PUBLICATIONS

Sikora, S., and Godzik, A., Combination of multiple alignment analysis and surface mapping paves a way for a detailed . . . , Prot Sci 2004;13:786-96.

Snijder, E., and Meulenberg, J., Arteriviruses, Fields' Virology; 1205-20.

Sofia, M., Carbohydrate-based combinatorial libraries, Mol Divers 1998;3:75-94.

Szent-Gyorgyi, et al., Cloning and characterization of new bioluminescent proteins, Jan. 1999;3600:4-11.

Takeda, S., et al., Construction of chimaeric processed immunoglobulin genes conatining mouse variable and human constant . . . , Nature, Apr. 1985;314:452-4.

Tietze, L. and Lieb, M. , Domino reactions for library synthesis of small molecules in combinatorial chemistry, Curr Biol Chem Biol 1998;2:263-71.

Ward, S., et al., Binding activities of a repertoire of single immunoglobulin variable domains secreted from *Escherichia coli*, Nature 1989;341:544-6.

Genbank, Accession #AY274119.3, SEQ ID No. 3.

Genome Sciences Centre. Release 2003, SEQ ID No. 4.

Cote, R., et al., Monoclonal antibodies and cancer therapy, J Cell Bio Chem;29:33-74.

* cited by examiner

Seq. ID No. 1. SARS cAMP-dependent kinase protein sequence (ORF3a-encoded):
MDLFMRFFTLXSITAQPVKIDNASPASTVHATATIPLQASLPFGWLVIGVAFLA
VFQSATKIIALNKRWQLALYKGFQFICNLLLLFVTIYSHLLLVAAGMEAQFLY
LYALIYFLQCINACRIIMRCWLCWKCKSKNPLLYDANYFVCWHTHNYDYCIP
YNSVTDTIVVTEGDGISTPKLKEDYQIGGYSEDRHSGVKDYVVVHGYFTEVY
YQLESTQITTDTGIENATFFIFNKLVKDPPNVQIHTIDGSSGVANPAMDPIYDEP
TTTTSVPL

Figure 2a

Seq. ID No. 2. SARS kinase-associated C2 domain (ORF3b-encoded):
MMPTTLFAGTHITMTTVYHITVSQIQLSLLKVTAFQHQNSKKTTKLVVILRIGT
QVLKTMSLYMAISPKFTTSLSLHKLLQTLVLKMLHSSSLTSLLKTHRMCKYT
QSTALQELLIQQWIQFMMSRRRLLACLCKHKKVSTNLCTHSFRKKQVR

Fig.3

ORF 3b

```
            *              20                  *             40                *            60                *            80
Arabidopsi : i-elvlveardlvaadirgtsdpyvr----vqy-----gekRqtTwvlyktTlqpkwnqtmefp----ddgsslelhvkdyntllp : 71
C_el       : i-tltvlcaggliakdktgksdpyvt----aqv-----gktlkrrtrihqelnpvwnekfhfechnstd--rikvrvwdtvkila     : 73
Danio      : l-tvsikeaknlvpmdpnglsdpyvk---lklipdpkseskqktkwiikcclnptwnetftfnlkesdkdrrlsveiwdwdl---    : 77
Human      : l-hvtvrdaknlipmdpnglsdpyvk---lklipdpknesKqktkwirstlnpqwnesftfklkpsdkdrrlsveiwdwdrttr    : 80
Takifugu   : l-hvtvgearnlipmdpnglsdpyvk---lkitpdpknetkqktrdirsslnpqwnesftfklkpsdkdrrlsvevwdwdr---    : 77
SARS       : mmpttlfagthitmttvyhitvsqiqlsllk

UNCHARACTERIZED ORF3 IN SARS-CORONAVIRUS IS A CYCLIC-AMP-DEPENDENT KINASE AND A TARGET FOR SARS THERAPY

RELATED APPLICATION

Benefit of priority under 35 U.S.C. 119(e) is claimed herein to U.S. Provisional Application No. 60/571,698, filed May 17, 2004. The disclosure of the above referenced application is incorporated by reference in its entirety herein.

STATEMENT REGARDING GOVERNMENT FUNDED RESEARCH

This invention was made with U.S. government support under the National Institutes of Health Grant No. GM53910. The U.S. government has certain rights in this invention.

SEQUENCE LISTING

The Sequence Listing is provided herein in accordance with 37 CFR §§ 1.821 through 1.825, and is submitted herewith as follows: (1) the sequence listing is provided for as a separate paper in accordance with 37 CFR § 1.821(c), and is incorporated herein by reference; and (2) the copy of the sequence listing referred to above is also submitted herewith in computer readable form in accordance with 37 CFR. § 1.821(e) and 37 CFR § 1.824.

FIELD OF THE INVENTION

The present invention relates to novel methods for identifying antiviral agents which selectively interfere with viral proteins that cause the unique infectivity activity of the SARS-coronavirus in comparison to other non-SARS strains of coronavirus. In particular, the present invention relates to screening assays that identify agents which selectively inhibit cyclic-AMP dependent protein kinase activity of the SARS-coronavirus ORF3. The present invention also relates to screening assays that identify agents which selectively inhibit the interaction between SARS-coronavirus cyclic-AMP dependent protein kinase and a calcium dependent targeting molecule. Therefore the agents identified using the assays of the invention may have utility as antiviral agents. The present invention also relates to treatments for sever acute affect the infectivity activity of the SARS-coronavirus. The present invention also relates to diagnostic assays for identifying and characterizing a strain of coronavirus as being one causing severe acute respiratory syndrome.

BACKGROUND

The coronaviruses are members of a family of enveloped viruses that replicate in the cytoplasm of animal host cells, and that are most commonly implicated with the common cold (B. N. Fields, D. M. Knipe, P. M. Howley, D. E. Griffin, Fields Virology (Lippincott Williams & Wilkins, Philadelphia, ed. 4, 2001); Holmes, K. V. 2001. Coronaviruses. In Fields' virology. D. Knipe, et al., editors. Lippincott Williams & Wilkins. Philadelphia, Pa., USA. 1187-1203). They are distinguished by the presence of a single-stranded plus-sense RNA genome about 30 kb in length that has a 5' cap structure and 3' polyadenylation tract. Upon infection of an appropriate host cell, the 5'-most open reading frame (ORF) of the viral genome is translated into a large polyprotein that is cleaved by viral-encoded proteases. Cleavage of this large polyprotein releases both structural and non-structural proteins. The coronavirus membrane contains three or four viral structural proteins. The membrane (M) glycoprotein is the most abundant structural protein; it spans the membrane bilayer three times, leaving a short $NH_2$-terminal domain outside the virus (or exposed luminally in intracellular membranes) and a long COOH terminus (cytoplasmic domain) inside the virion. The spike protein (S) is a type I membrane glycoprotein that constitutes the peplomers. The small envelope protein (E) has been detected as a minor structural component in avian infectious bronchitis virus (IBV), transmissible gastroenteritis virus (TGEV), and mouse hepatitis virus (MHV) particles, but it has not been extensively characterized. Some coronaviruses also contain a hemagglutinin-esterase protein (HE). Coronaviruses attach to host cells through the spike (S) glycoprotein. The viral membrane proteins, including the major proteins S (Spike) and M (membrane), are inserted into the endoplasmic reticulum (ER) Golgi intermediate compartment while full length replicated RNA plus strands assemble with the N (nucleocapsid) protein. This RNA protein complex then associates with the M protein embedded in the membranes of the ER, and virus particles form as the nucleocapsid complex buds into the lumen of the ER. The virus then migrates through the Golgi complex and eventually exits the cell, likely by exocytosis (B. N. Fields, D. M. Knipe, P. M. Howley, D. E. Griffin, Fields Virology (Lippincott Williams & Wilkins, Philadelphia, ed. 4, 2001)). The site of viral attachment to the host cell resides within the S protein.

The coronavirus large polypeptide is also cleaved to release several nonstructural proteins, including an RNA-dependent RNA polymerase (Rep) and an adenosine triphosphatase (ATPase) helicase (Hel). These proteins, in turn, are responsible for replicating the viral genome as well as generating nested transcripts that are used in the synthesis of the viral proteins.

The coronaviruses include a large number of viruses that infect different animal species. The predominant diseases associated with these viruses are respiratory and enteric infections, although hepatic and neurological diseases also occur. Human coronaviruses identified in the 1960s (including the prototype viruses HCoV-OC43 and HCoV-229E) are responsible for up to 30% of respiratory infections (S. H. Myint, in The Coronaviridae, S. G. Siddell, Ed. (Plenum, New York, 1995), pp. 389-401. Marra M A, Jones S J, Astell C R, Holt R A, Brooks-Wilson A, Butterfield Y S, et al. The genome sequence of the SARS-associated coronavirus. Science 2003; 300:1399-1404). Coronaviruses are currently classified into three antigenic groups: group 1 and 2 include mammalian coronaviruses, and group 3 encompasses avian coronaviruses. Human coronaviruses associated with common cold-like diseases are included in both group 1 (CoV-229E) and 2 (CoV-OC43) (Siddell S. The coronaviridae. New York: Plenum Press; 1995).

A novel human coronavirus has been isolated from the oropharyngeal specimens of patients with severe acute respiratory syndrome ("SARS"), and termed SARS-associated coronavirus [SARS-CoV] (See; Peiris J, et al. Lancet 2003; 361:1319-25; and see Ksiazek T G, et al. N Engl J Med 2003; 348:1953). Experimental infection of macaques has confirmed that the SARS-CoV is the cause of SARS (See; Fouchier R A, et al. Nature 2003; 423:240; and see Kuiken T, et al. Lancet 2003; 362:263-70). Sequence analysis of the complete genome of SARS-CoV has shown an RNA molecule of about 29,750 bases in length, with a genome organization similar to that of other coronaviruses (Ruan Y J, et al. Lancet 2003; 361:1779-85; Rota P A, et al. Science 2003; 300:1394-9. Marra Mass., et al. Science 2003; 300:1399-

1404). In spite of this similar organization, the SARS-CoV RNA sequence is only distantly related to that of previously characterized coronaviruses (Ruan Y J, et al. Lancet 2003; 361: 1779-85). Consequently, whether the SARS-CoV has "jumped" from a nonhuman host reservoir to humans and the molecular basis of such a jump remain unanswered questions (Cyranoski D, Abbott A. Nature 2003; 423:467). Some biologic features of the SARS-CoV described in vivo and in vitro differ from those of other coronaviruses previously identified. Among these features are the peculiar tropism of the virus for Vero cells (a continuous cell line established from monkey kidney epithelial cells), its capacity for growth at 37° C. (while other respiratory coronaviruses grow at lower temperatures), and its ability to infect lower respiratory tract tissues (Holmes K V. J Clin Invest 2003; 111:1605-9). These aspects render the molecular and biologic characterization of SARS-CoV important not only for understanding the determinants of its pathogenic potential but also for planning rational strategies of antiviral therapy and vaccination. Particularly important is the unique infectivity of SARS-CoV over other coronaviruses, which at least partially accounts for the severity of SARS in comparison to the common cold.

SUMMARY OF THE INVENTION

The invention is based in part, on the Applicants' discovery that (1) the ORF3 of SARS-coronavirus codes for a protein having cyclic-AMP dependent protein kinase activity (ORF3a) and also codes for a calcium dependent targeting molecule (ORF3b); (2) that the cyclic-AMP dependent protein kinase and the calcium dependent targeting module interact; and (3) the cyclic-AMP dependent protein kinase is responsible for the unique infectivity characteristics of SARS-cronavirus compared to other non-SARS strains of coronavirus.

The present invention further encompasses the novel agents identified by the screening assays described herein. The invention relates to therapeutic modalities and pharmaceutical compositions for the treatment of viral infections using ORF3 proteins as the target for intervention. The present invention more particularly relates to therapeutic modalities and pharmaceutical compositions for the treatment of SARS-corona virus infection by targeting the activity of ORF3 protein products.

The present invention also relates to the use of antiviral agents identified by the present invention in combinatorial therapies with other known antiviral agents to inhibit viral infectivity. The agents identified by the screening assays of the present invention also have utility in reducing the virus's rate of infectivity of a cell, and thus would be useful to increase the efficacy of current therapies to threat severe acute respiratory syndrome.

BRIEF DESCRIPTION OF THE DRAWINGS

FIG. 2a illustrates the protein sequence of the SARS cyclic-AMP dependent protein kinase of ORF3a (SEQ ID No.: 1).

FIG. 2b illustrates the protein sequence of the C2 domain or calcium dependent membrane targeting module of ORF3b (SEQ ID No.: 2).

FIG. 3 illustrates the amino acid sequence of ORF3a (SEQ ID No.: 1) compared to the amino acid sequences of protein kinases from other organisms. The catalytic sites and the ADP-binding P-loop residues are highlighted. SEQ ID Nos.: 5-14 are, *Caenorhabditis, Aspergillus, Saccharomyces, Cryptococcus, Leishmania, Amblyomma, Anopheles, Danio, Xenopus* and *Homo sapiens*, respectively.

FIG. 6 illustrates the amino acid sequence of ORF3b (SEQ ID No.: 2) compared to the amino acid sequences from other species. The conserved surface cluster is highlighted. SEQ ID Nos.: 17-21 are *Arabidopsis, Caenorhabditis elegans, Danio, Homo sapiens* and *Fugu rubripes* (recently renamed takifigu), respectively.

DETAILED DESCRIPTION OF THE INVENTION

Figure 1:
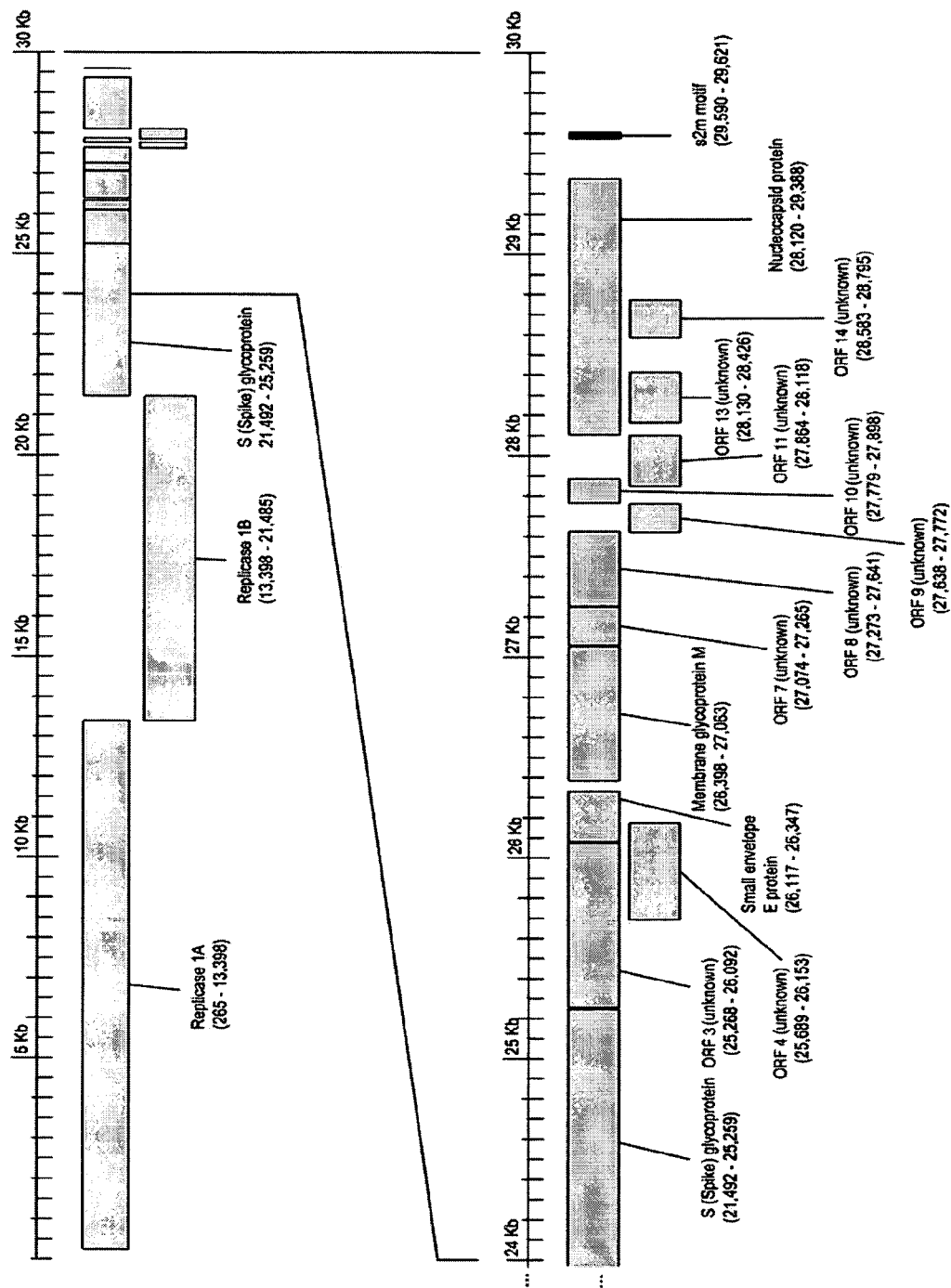
FIG. 1 is a map of the open reading frames (ORF) of a common SARS coronavirus genome sequence.

The present invention relates to novel methods for identifying antiviral agents which selectively interfere with viral proteins that cause the unique infectivity activity of the SARS-coronavirus in comparison to other non-SARS strains of coronavirus. In particular, the present invention relates to screening assays that identify agents which selectively inhibit cyclic-AMP dependent protein kinase activity of the SARS-coronavirus ORF3. The present invention also relates to screening assays that identify agents which selectively inhibit the interaction between SARS-coronavirus cyclic-AMP dependent protein kinase and a calcium dependent targeting molecule. Therefore the agents identified using the assays of the invention may have utility as antiviral agents. The present invention also relates to treatments for severe acute respiratory syndrome caused by a coronavirus, and particularly to treatments that affect the infectivity activity of the SARS-coronavirus. The present invention also relates to diagnostic assays for identifying and characterizing a strain of coronavirus as being one causing severe acute respiratory syndrome.

Abbreviations and Terms

In accordance with the present invention and as used herein, the following terms and abbreviations are defined with the following meanings unless explicitly stated otherwise. These explanations are intended to be exemplary only. They are not intended to limit the terms as they are described or referred to throughout the specification. Rather, these explanations are meant to include any additional aspects and/or examples of the terms as described and claimed herein.

The following abbreviations are used herein:

As used herein, the term "screening" or "to screen" refers to a process in which a large number of potentially useful agents are processed in the methods of the invention.

As used herein, the term "to target" means to inhibit, block or prevent gene expression, enzymatic activity or interaction with other cellular or viral factors.

As used herein, the term "treating or preventing severe acute respiratory syndrome or SARS" means to inhibit SARS-coronavirus infectivity, or to prevent SARS-coronavirus from establishing itself in its host, and to ameliorate or alleviate the symptoms of the disease caused by SARS-coronavirus infection. The treatment is considered therapeutic if there is a reduction in viral load, decrease in mortality and/or morbidity.

As used herein, the term "treating or preventing viral infection" means to inhibit virus infectivity of a cell, or to prevent the virus from establishing itself in its host, and to ameliorate or alleviate the symptoms of the disease caused by viral infection. The treatment is considered therapeutic if there is a reduction in viral load, decrease in mortality and/or morbidity.

As used herein, the term "pharmaceutically acceptable carrier" refers to a carrier medium that does not interfere with the effectiveness of the biological activity of the active ingredient, is chemically inert and is not toxic to the patient to whom it is administered.

The term "therapeutic agent" refers to any molecule compound or treatment, preferably an antiviral, that assists in the treatment of a viral infection or the diseases caused thereby.

The term "candidate compound" refers to any molecule that potentially acts as a ligand, agonist or antagonist or ligand in the screening methods disclosed herein. A candidate compound can be a naturally occurring macromolecule, such as a polypeptide, amino acid, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

The term "detectable label" refers to any moiety that can be selectively detected in a screening assay. Examples include without limitation, radiolabels, (e.g., $^3H$, $^{14}C$, $^{35}S$, $^{125}I$, $^{131}I$), affinity tags (e.g. biotin/avidin or streptavidin, binding sites for antibodies, metal binding domains, epitope tags, FLASH binding domains—See U.S. Pat. Nos. 6,451,569; 6,054,271; 6,008,378 and 5,932,474—glutathione or maltose binding domains) fluorescent or luminescent moieties (e.g. fluorescein and derivatives, GFP, rhodamine and derivatives, lanthanides etc.), and enzymatic moieties (e.g. horseradish peroxidase, beta.-galactosidase, beta.-lactamase, luciferase, alkaline phosphatase). Such detectable labels can be formed in situ, for example, through use of an unlabeled primary antibody which can be detected by a secondary antibody having an attached detectable label.

The term "functional fragment" refers to a portion of a full-length ORF3a and/or ORF3b polypeptide that retains at least one biological activity characteristic of the full-length polypeptide. A functional fragment can contain, for example, at least about 6, 8, 10, 12, 15, 20, 25, 30, 35, 40, 50, 60, 70, 80, 90, 100, 110, 125, 150, 200, 250, 300, 400, 500, 600, 700, 800, 900, 950 or more amino acids of a polypeptide. The remaining amino acid sequence is identical to, or exhibits substantial identity to, the corresponding positions in the naturally-occurring sequence.

As used herein, the term "functionally expressed" refers to a coding sequence which is transcribed, translated, post-translationally modified (if relevant), and positioned in a cell such that the protein provides the desired function. With reference to a reporter cassette, functional expression generally means production of a sufficient amount of the encoded cell surface reporter protein to provide a statistically significant detectable signal to report transcriptional effects of a reporter polynucleotide.

"Naturally fluorescent protein" refers to proteins capable of forming a highly fluorescent, intrinsic chromophore either through the cyclization and oxidation of internal amino acids within the protein or via the enzymatic addition of a fluorescent co-factor. Typically such chromophores can be spectrally resolved from weakly fluorescent amino acids such as tryptophan and tyrosine. Endogenously fluorescent proteins have been isolated and cloned from a number of marine species including the sea pansies *Renilla reniformis*, *R. kollikeri* and *R. mullerei* and from the sea pens *Ptilosarcus*, *Stylatula* and *Acanthoptilum*, as well as from the Pacific Northwest jellyfish, *Aequorea victoria*; Szent-Gyorgyi et al. (SPIE conference 1999), D. C. Prasher et al., Gene, 111:229-233 (1992) and red and yellow fluorescent proteins from coral. A variety of mutants of the GFP from *Aequorea victoria* have been created that have distinct spectral properties, improved brightness and enhanced expression and folding in mammalian cells compared to the native GFP, (Green Fluorescent Proteins, Chapter 2, pages 19 to 47, edited Sullivan and Kay, Academic Press, U.S. Pat. Nos. 5,625,048 to Tsien et al., issued Apr. 29, 1997; 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type proteins and are preferred for use as reporter genes in the present invention. Preferred naturally fluorescent proteins include without limitation, EGFP, YFP, Renilla GFP and DS red.

The term "nucleic acid molecule," as used herein, refers to a polynucleotide of natural or synthetic origin. A nucleic acid molecule can be single- or double-stranded genomic DNA, cDNA or RNA, and can represent a sense strand, an antisense strand, or both. Accordingly, a designated sequence identifier, unless specified otherwise, is intended to refer to the single-stranded molecule having the recited sequence, the single-stranded complement of the recited sequence, or a double stranded (or partially double-stranded) molecule in which one strand has the recited sequence. A nucleic acid molecule can optionally include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a hybridizing nucleic acid molecule is desired.

The term "isolated nucleic acid molecule," as used herein, refers to a nucleic acid molecule that is substantially purified away from other nucleic acid molecules and other molecules, such as protein molecules, carbohydrate molecules, and lipid molecules, that normally occur together with the nucleic acid molecule in the cell or virus in which the nucleic acid molecule is found. The term "isolated nucleic acid molecule" does not require any particular degree of purity, but does require that the activity of a preparation of the isolated nucleic acid molecule be primarily due to the isolated nucleic acid molecule and not to any other nucleic acid molecules, protein molecules, or other molecules found in the preparation. Unless otherwise limited, the term "isolated nucleic acid molecule" does not preclude the attachment of additional bases to either the 5'-end or the 3'-end of the molecule.

The term "ORF3" refers to the open reading frame of the SARS-coronavirus, and can be used to refer to ORF3a and ORF3b combined.

The term "ORF3a" refers to the open reading frame of the SARS-coronavirus corresponding to the cyclic-AMP dependent protein kinase viral protein of Applicant's discovery, and is presented herein as SEQ ID No.: 1 and SEQ ID No. 15.

The term "ORF3b" refers to the open reading frame of the SARS-coronaviras corresponding to the Ca.sup.2+ dependent membrane targeting module viral protein of Applicant's discovery, and in presented herein as SEQ ID No.: 2 and SEQ ID No.: 16.

A "reporter gene" includes any gene that directly or indirectly produces a specific reporter gene product, detectable label, enzymatic moiety, or cellular phenotype, such as drug resistance that can be used to monitor transcription of that gene. Preferred reporter genes include proteins with an enzymatic activity that provides enzymatic amplification of gene expression such as .beta.-lactamase, luciferase, .beta.-galactosidase, catalytic antibodies and alkaline phosphatase. Other reporter genes include proteins such as naturally fluorescent proteins or homologs thereof cell surface proteins or the native or modified forms of an endogenous gene to which a specific assay exists or can be developed in the future. Preferred reporter genes for use in the present invention provide for multiplexed analysis.

The term "peptide similar to . . . " means a peptide having the same or substantially the same interaction with another specified molecule as the peptide in reference.

Since the list of technical and scientific terms cannot be all encompassing, any undefined terms shall be construed to have the same meaning as is commonly understood by one of skill in the art to which this invention belongs.

ORF3 (FIG. 1; base pairs 25,268 to 26,092 of SEQ ID Nos.: 3 and 4) encodes a predicted protein of 274 amino acids. (See, Marra, M A et al, The Genome Sequence of the SARS-Associated Coronavirus, *Science* 300, 1399-1404 (2003). The SARS genome presented in Marra et al. has been deposited with Genbank (Accession #AY274119.3, SEQ ID No.:3) and with Canada's Michael Smith Genome Sciences Centre (Release 3 2003/04/29, SEQ ID No.:4).) Marra, M A, et al. performed sequence analysis on the Tor2 strain of SARS-CoV and found that ORF3 lacks significant BLAST, FASTA, or PFAM similarities to any known protein; analysis of the N-terminal 70 amino acids with SignalP provided weak evidence for the existence of a signal peptide and a cleavage site (probability 0.540); and both TMpred (27) and TMHMM predict the existence of three transmembrane regions spanning approximately residues 34 to 56, 77 to 99, and 103 to 125. The most likely model from these analyses is that the C-terminus and a large 149-amino acid N-terminal domain would be located inside the viral or cellular membrane. The C-terminal (interior) region of the protein may encode a protein domain with ATP-binding properties (ProDom ID PD037277).

Applicants used a Fold and Function Assignment System ("FFAS" The Burnham Institute, La Jolla, Calif., http://bioinformatics.ljcrf.edu/FFAS/) for protein structure prediction, modeling and model analysis to identify ORF3as having a subunit coding for a homologue to cyclic-AMP dependent protein kinase ("ORF3a" SEQ ID No.: 1 and 15 and FIG. 2*a*) and a subunit coding for a Ca.sup.2+ dependent membrane targeting module that associates with the protein kinase ("ORF3b" SEQ ID No.: 2 and 16 and FIG. 2*b*). Applicants also used the following programs:

1. 3D-PSSM: http://www.sbg.bio.ic.ac.uk/~3dpssm/
2. Modeller 6v2
3. Gramm hydrophobic docking software
4. Swiss PDB Viewer
5. T-COFFEE multiple alignment program v1.37
6. Robetta structural prediction: http://robetta.bakerlab.org/
7. FATCAT: http://ffas.ljcrf.edu/fatcat/fatcatpair.html
8. New Method of phylogenetic trace: reference: Sikora S and Godzik, Prot. Sci, 2004

Those of ordinary skill in the art will readily use these and other prediction algorithms all within the spirit of the current invention.

Figure 4:
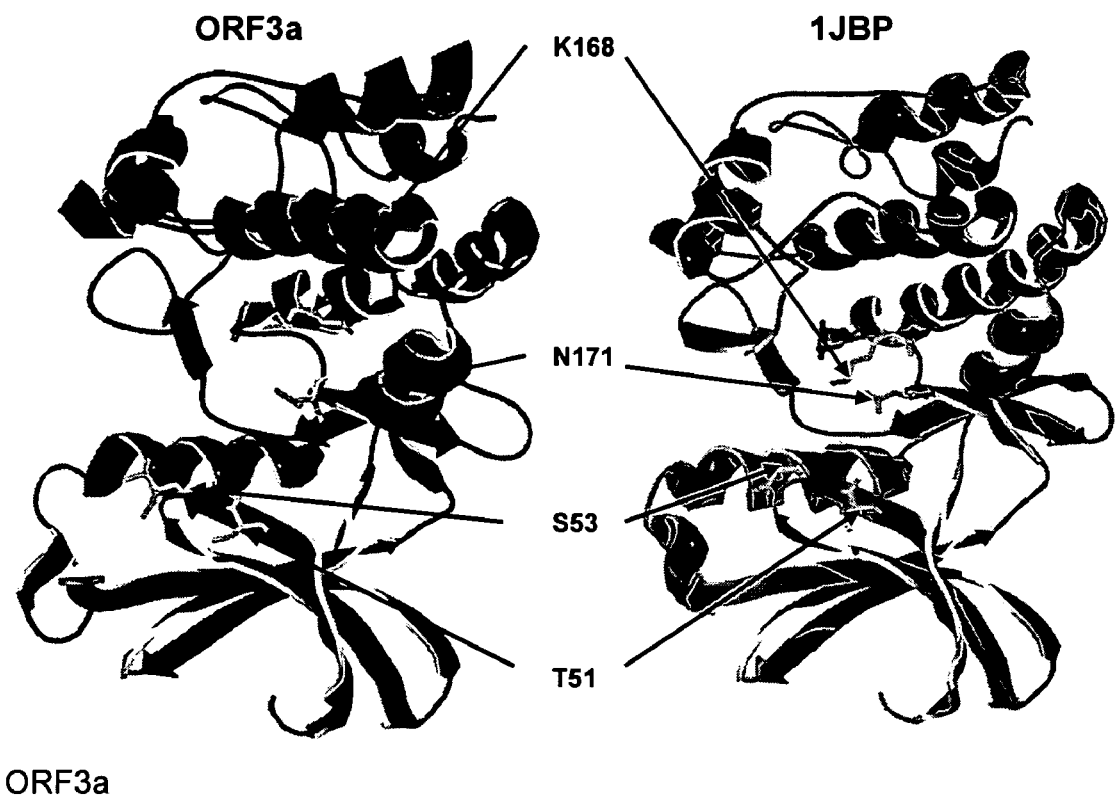
FIG. 4 is a three dimensional model of the ORF3a compared to a protein kinase from a mouse.
Figure 5:
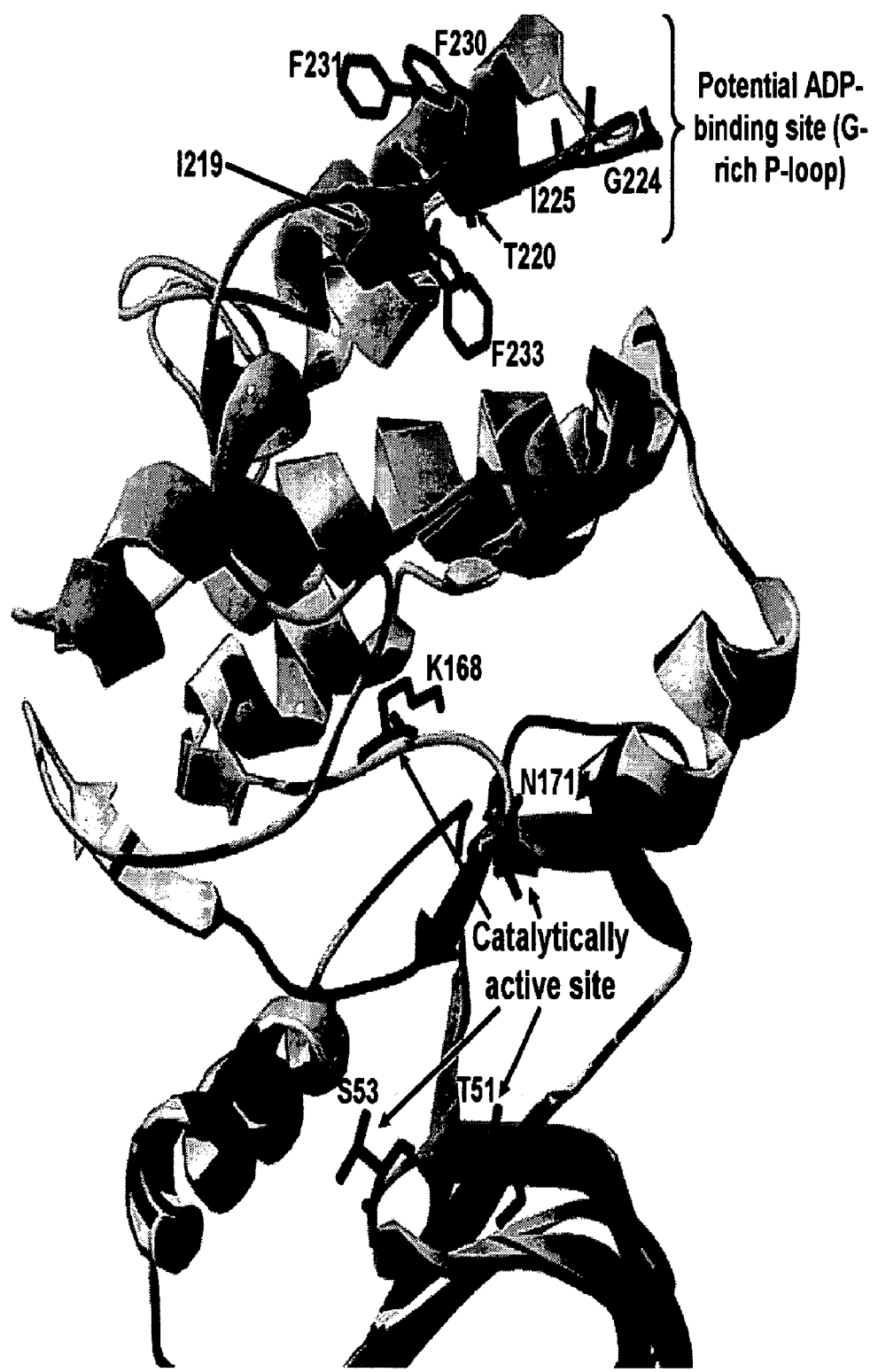
FIG. 5 further illustrates the three dimensional structure of ORF3a and highlights the ADP-binding loop and the catalytic activity site.

Applicants have also compared the protein sequence of ORF3a with the sequences of a variety of other known cAMP-dependent protein kinases. As is seen in FIG. 3, both the catalytic domain and the ADP binding loop are present in ORF3a, consistent with these other known protein kinases. (SEQ ID Nos.: 1, 5-14). Structural comparison of ORF3a with the mouse homologue 1JBP, shows remarkable similarity. FIG. 4. Residues T51, S53, K168 and N171 from the catalytic domain of these cAMP-dependent protein kinases are highlighted, and, as is illustrated in FIGS. 3 and 4, this catalytic domain is conserved from eukaryotic organisms to SARS-CoV. In FIG. 5, both the catalytic domain and the ADP binding site are illustrated, and, as is illustrated in FIGS. 3 and 5, the ADP binding site P-loop is also conserved. Previous genetic studies of different SARS-CoV strains reveal a very high rate of mutations and a large degree of divergence between corresponding proteins from different coronavirus strains; however, such rates of mutation are not found in ORF3 of the different SARS-CoV. Other coronavirus strains have neither the infectivity profile of SARS-CoV, nor do these strains contain an ORF3. Thus, applicants' have discovered that ORF3a and ORF3b code for a protein kinase and an associated Ca.sup.2+-dependent targeting molecule that accounts for the unique infectivity of SARS-CoV over other strains of coronavirus.

Figure 7:
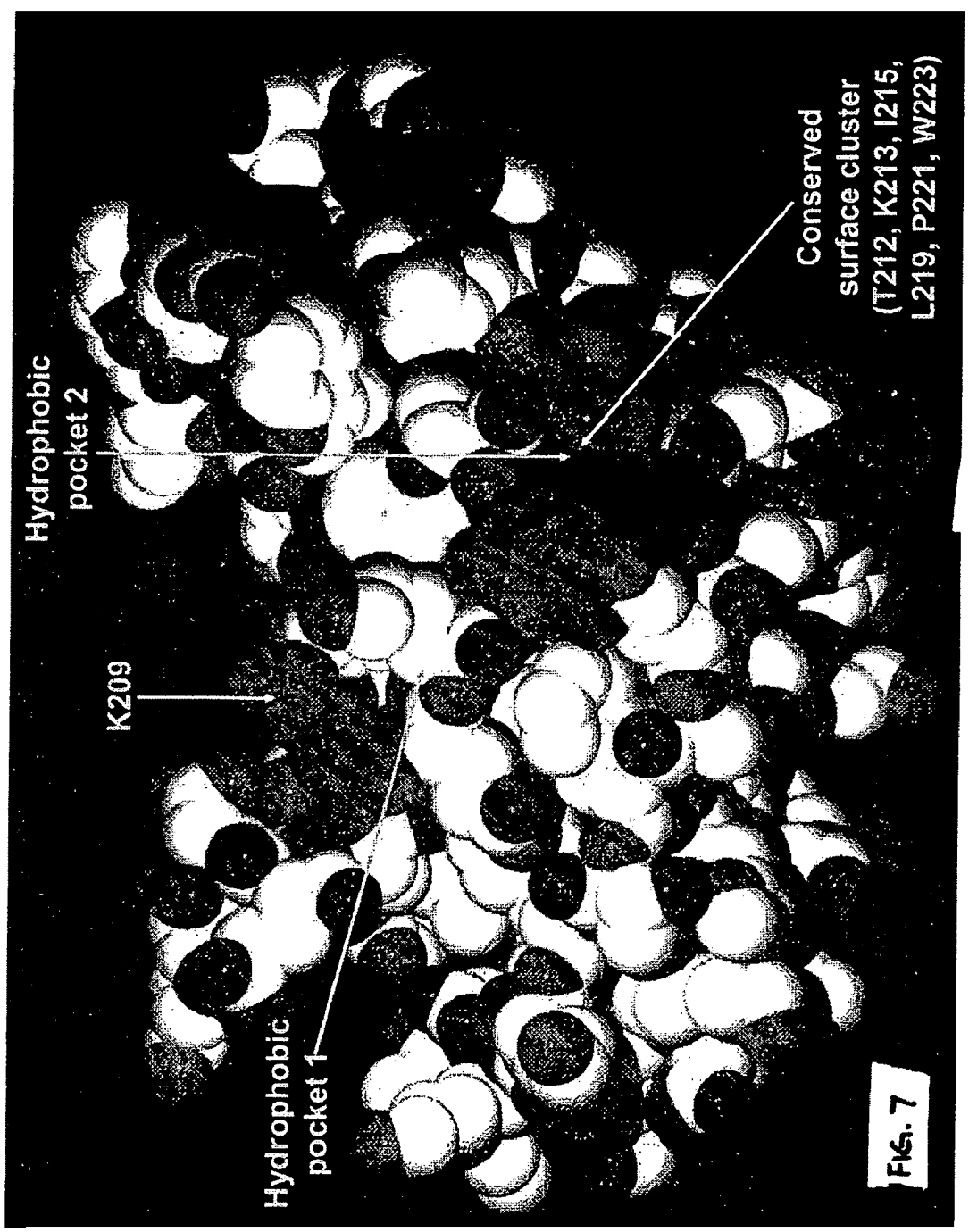
FIG. 7 is a three dimensional molecular model of ORF3b, highlighting the conserved surface cluster and hydrophobic pockets 1 and 2.

Sequence analysis of ORF3b reveals that the protein has a conserved surface cluster comprising two hydrophobic clusters. FIG. 6 (SEQ ID Nos.: 2, 17-21) and FIG. 7. These conserved hydrophobic pockets within ORF3b participate in protein-protein interaction and are responsible for the interaction with ORF3a. Using GRAMM software, Applicants determined that loops 1 and 2 of ORF3a dock with the hydrophobic pockets of ORF3b (GRAMM docking score −444). Thus, applicants have discovered that the $Ca^{2+}$-dependant targeting module (ORF3b) is usually part of the cAMP-dependant protein kinase (ORF3a), thereby interacting with each other to increase the infectivity of SARS-CoV over that of other strains of coronavirus.

Cyclic AMP-dependant kinases are widely used by many viruses for increased infectivity. For example, it is known that HIV incorporates a human cAMP-dependent kinase into its virion to regulate infectivity (See Cartier, C et al., J. Biol. Chem., 278:35211-35219). Using techniques well know in the art, it can be shown that the cAMP-dependant protein kinase of SARS-CoV is similarly used for increased infectivity over other strains of coronavirus.

Accordingly, one aspect of the present invention is a method of screening a candidate compound for the inhibition of the ORF3a cAMP-dependent SARS coronavirus protein kinase activity comprising:

(1) providing a candidate compound;
(2) performing an assay of the activity of the ORF3a cAMP-dependent SARS coronavirus protein kinase in the presence and in the absence of varying concentrations of the candidate compound; and
(3) determining whether the candidate compound inhibits the activity of the ORF3a cAMP-dependent SARS coronavirus protein kinase.

The inhibition of the activity of the ORF3a cAMP-dependent coronavirus can be determined either directly, by measuring the activity of the kinase in phosphorylating a suitable protein substrate, or indirectly, by measuring the effect on infectivity, as described above.

Among the compounds that are candidates for screening for inhibition of the activity of the ORF3a cAMP-dependent SARS coronavirus protein kinase are compounds that inhibit the corresponding cAMP-dependent kinase of HIV virus (Cartier et al., *J. Biol. Chem.* 278; 35211 (2003)) and homologues, analogues, and isosteres of such compounds. These include fasudyl ((1-(5-isoquinolinesulphonyl)-homopiperazine) and other cAMP-dependent kinase inhibitor agents.

Because the unusual infectivity of SARS coronavirus is correlated with the activity of the ORF3a cAMP-dependent protein kinase, as well as the X1 kinase associated protein X2, encoded by ORF3b, and because SARS, as well as other coronaviruses, has a significant rate of mutation, another aspect of the invention is a method of correlating polymorphisms in either ORF3a or ORF3b with the infectivity of a SARS strain. In general, this method comprises the steps of:

(1) isolating a SARS strain;
(2) determining the sequence of the ORF3a and ORF3b of the RNA genome of the isolated SARS strain;
(3) determining the infectivity of the isolated SARS strain relative to the infectivity of a reference SARS strain; and
(4) correlating a difference in infectivity of the isolated SARS strain and of the reference SARS strain with a polymorphism in one or both of ORF3a and ORF3b.

The reference strain can be the strain whose complete genomic sequence was determined in M. A. Marra et al., "The Genome Sequence of the SARS-Associated Coronavirus," *Science* 300: 1399-1404 (2003).

The RNA genome of the isolated strain can be sequenced by converting the RNA to cDNA by means of a combined random priming and oligo (dT priming strategy. Size-selected cDNA products can be cloned, and single sequence reads can be generated from each end of the insert from randomly chosen clones. The resulting sequences can be assembled by standard techniques to determine the sequence of the ORF3a and ORF3b of the isolated SARS strain.

This method can be used to build up a table of correlations between polymorphisms and infectivity, so that, when a potentially new SARS strain is isolated from a patient suspected of having SARS infection, the table of correlations can then be used to determine appropriate public health measures, such as the appropriate period of quarantine and the extent of quarantine of the patient's contacts. The table of correlations can be stored in a computer-readable database such as on a hard drive, a CD-ROM, or a floppy disc, or on a web-accessible database.

The present invention also relates to screening assays to identify those compounds which would target cyclic-AMP dependent protein kinase of ORF3a; the interactions between the cAMP-dependent protein kinase and the Ca.sup.2+ dependent targeting module of ORF3b, and more specifically the cAMP dependent protein kinase dependent infectivity characteristics of SARS-CoV. In one embodiment of the invention, an important component of the screening assays of the present invention is the nucleotide coding sequences encoding ORF3 viral proteins, polypeptides and peptides. In particular, the present invention encompasses nucleotide coding sequences encoding peptide fragments corresponding to the cAMP-dependent protein kinase activity and to the interaction surfaces between ORF3a and ORF3b. The present invention further encompasses (a) nucleic acid vectors that contain any of the foregoing encoding sequences and/or their complements; (b) expression vectors that contain any of the foregoing coding sequences operatively associated with a regulatory element that directs the expression of the coding sequences in the host cell; and (c) genetically engineered host cells that contain any of the foregoing coding sequences operatively associated with a regulatory element that directs the expression of the coding sequences in the host cell.

The invention encompasses nucleotide coding sequences that encode ORF3 proteins, peptide fragments and fusion proteins. In a preferred embodiment, the invention encompasses nucleotide coding sequences encoding the ORF3a amino acid sequence as shown in FIG. 2a, peptide fragment and fusion proteins containing that amino acid sequence. In a further embodiment, the present invention encompasses nucleotide sequences which encode ORF3 mutations and peptide fragments and fusion proteins that comprise these ORF3 mutants.

Similarly, the invention also encompasses an isolated nucleic acid molecule that includes the ORF3 open reading frame, the ORF3a open reading frame, or the ORF3b open reading frame. The invention further encompasses an isolated nucleic acid molecule that encodes the same polypeptide sequence as the ORF3 open reading frame, the ORF3a open reading frame, or the ORF3b open reading frame. The invention still further encompasses an isolated nucleic acid molecule that encodes a polypeptide sequence that varies from the polypeptide sequence encoded by the ORF3 open reading frame, the ORF3a open reading frame, or the ORF3b open reading frame, by one or more conservative amino acid substitutions, preferably from 1 to 20 conservative amino acid substitutions, more preferably from 1 to 10 amino acid substitutions. It is a well-established principle of protein and peptide chemistry that certain amino acid substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments. One such example of a conservative change is in the ORF3 amino acid sequence wherein the applicants have found that residue 11 can be either a glycine (G) or an arginine (R).

The invention also encompasses: (a) nucleic acid vectors that contain any of the foregoing ORF3 coding sequences and/or their complements (i.e., antisense); (b) expression vectors that contain any of the foregoing ORF3 coding sequences operatively associated with a regulatory element that directs the expression of the coding sequences; and (c) genetically engineered host cells that contain any of the foregoing ORF3 coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to inducible promoters, such as heat shock promoters, galactose inducible promoters, viral promoters, such as the promoter of tobacco mosaic virus (TMV), cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast alpha.-mating factors.

EXAMPLES

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about 103, 105 or 107 different compounds, which can be assayed simultaneously or sequentially.

Generally, the nomenclature used herein and the laboratory procedures in cell culture, molecular genetics, and nucleic acid chemistry and hybridization described are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document, as well as: Maniatis et al., Molecular Cloning: A Laboratory Manual (1989), 2nd Ed., Cold Spring Harbor, N.Y.; and Berger and Kimmel, Methods in Enzymology, Volume 152, Guide to Molecular Cloning Techniques (1987), Academic Press, Inc., San Diego, Calif., which are incorporated herein by reference. Oligonucleotides can be synthesized on an Applied Bio Systems oligonucleotide synthesizer according to specifications provided by the manufacturer. The procedures are believed to be well known in the art and are provided for the convenience of the reader. All the information contained therein is incorporated herein by reference.

Example 1

It can be shown that ORF3a and ORF3b are necessary for the increased infectivity of SARS-CoV over other coronaviruses using recombinant techniques and viral infectivity assays. For example, using an inhibitor of protein kinase, SARS-CoV can be assayed for infectivity along with a non-SARS causing strain of coronavirus. In this assay SARS-CoV and standard coronaviruses are incubated a cell line such as Vero E6, in the presence or absence of a known inhibitor specific for protein kinase. Following incubation, the viral inoculum is removed and carboxymethylcellulose (Sigma Chemical Corp., St. Louis, Mo.) overlay with DMEM supplemented with fetal calf serum added to each well. The cells are then stained and the plaques counted. The virus titer is calculated in PFU per milliliter. Here, the inhibition of ORF3a, causes the rate infectivity of SARS-CoV to resemble that of non-SARS strains of coronavirus. Thus, the ORF3a product is accountable for the unique and higher rate of infectivity seen in SARS-CoV as compared to non-SARS coronavirus.

Example 2

In a variation of example 1, above, candidate compounds can be screened for their effect on the infectivity of SARS-CoV. Candidate compounds shown to inhibit the infectivity of SARS-CoV are useful as anti-viral compounds for the treatment of SARS.

In this assay, Vero E6 cells are plated in duplicate in a multiwell plate and are exposed to either SARS-CoV; non-SARS strains of coronavirus, or media alone. In addition, each of the duplicate wells either contains a candidate compound, or not such that a comparison of each cell/virus environment can be assessed in the presence and absence of said test compound. Following incubation, the viral inoculum is removed and carboxymethylcellulose (Sigma Chemical Corp., St. Louis, Mo.) overlay with DMEM supplemented with fetal calf serum added to each well. The cells are then stained and the plaques counted. The virus titer is calculated in PFU per milliliter.

Candidate compounds that reduce the PFU per milliliter of a SARS-CoV well compared to a SARS-CoV well having no candidate compound are useful anti-viral agents for reducing the rate of infectivity of SARS-CoV. Furthermore, candidate compounds that reduce the PFU per milliliter of a SARS-CoV well to a PFU per milliliter more similar to a non-SARS coronavirus well or a media alone well are also desirable as an anti viral agent for significantly reducing or stopping the rate of infectivity for the SARS-CoV.

Example 3

In a further example, candidate compounds are screened for their effect on the activity of cAMP-dependent protein kinase from SARS-CoV. Those candidate compounds determined to reduce or inhibit cAMP dependent protein kinase activity in the SARS-CoV are useful as anti-viral agents that reduce or eliminate the infectivity of SARS-CoV.

Vero E6 cells are plated in multiple wells of a in a multiwell plate and are exposed to either SARS-CoV, or media alone. In addition, each of the wells either contains a candidate compound, or not such that a comparison of each cell/virus environment can be assessed in the presence and absence of said test compound. Virus particles or subtilisin-treated virions are then lysed and incubated in appropriate buffer in the presence of a cAMP-dependent protein kinase substrate such as Kemptide. PKA kinase activity is measured by counting the incorporation of [−32P]ATP in Kemptide. Basal phosphorylation levels for the wells having SARS-CoV or having media alone is measured in the absence of Kemptide.

Candidate compounds that abolish the incorporation of [−32P]ATP within the substrate in wells having SARS-CoV are useful as anti-viral agents.

Example 4

In a further example, candidate compounds are screened for the ability to inhibit the interaction between the ORF3a product and the ORF3b product. Those candidate compounds determined to disrupt such activity are useful as anti-viral agents that reduce or eliminate the infectivity of SARS-CoV.

Vero E6 cells are plated in multiple wells of a in a multiwell plate and are exposed to either SARS-CoV, or media alone. In addition, each of the wells either contains a candidate compound, or not such that a comparison of each cell/virus environment can be assessed in the presence and absence of said test compound. Following incubation, the lysates of each well are recovered and are assessed using standard western blot techniques. In short, the lysates are purified and are separated using gel electrophoresis. The separated product can then be transferred to nitrocellulose and exposed to a two stage antibody detection system wherein said first antibody is raised against an ORF3 protein product, preferably ORF3a and wherein said second antibody is raised against the first and has an fluorescent label useful for detection.

In this screening assay, the detection of a lysate from a well having cells only or having SARS-CoV and a candidate compound that does not inhibit the interaction between the ORF3a product and the ORF3b product will be at a higher position on the gel than the detection of a lysate from a well having SARS-CoV and a candidate compound that inhibits the interaction between the ORF3a and ORF3b products. Candidate compounds that inhibit this interaction are useful as anti-viral agents for the inhibition of the interaction of ORF3a product with ORF3b product.

Antibodies that define the ORF3 gene products are within the scope of this invention, and include antibodies capable of specifically recognizing one or more ORF3 gene product epitopes. Such antibodies may include, but are not limited to, polyclonal antibodies, monoclonal antibodies (mAbs), humanized or chimeric antibodies, single chain antibodies, Fab fragments, F(ab').sub.2 fragments; fragments produced by a Fab expression library, anti-idiotypic (anti-Id) antibodies, and epitope-binding fragments of any of the above. Such antibodies may be used, for example, in the detection of an ORF3 gene product in a biological sample, including, but not limited to, cell lysates, blood plasma and serum. Alternatively, the antibodies may be used as a method for the inhibition of ORF3 gene products activity.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256: 495-497; and U.S. Pat. No. 4,376,110), the human B-cell hybridoma technique (Kosbor et al., 1983, Immunology Today 4: 72; Cole et al., 1983, Proc. Natl. Acad. Sci. USA 80: 2026-2030), and the EBV-hybridoma technique (Cole et al., 1985, Monoclonal Antibodies And Cancer Therapy, Alan R. Liss, Inc., pp. 77-96). Such antibodies may be of any immuoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81: 6851-6855; Neuberger et al., 1984, Nature, 312: 604-608; Takeda et al., 1985, Nature, 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242: 423-426; Huston et al., 1988, Proc. Natl. Acad. Sci. USA 85. 5879-5883; and Ward et al., 1989, Nature 334: 544-546) can be adapted to produce single chain antibodies against NS5A gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab').sub.2 fragments which can be produced by pepsin digestion of the antibody molecule and the Fab fragments which can be generated by reducing the disulfide bridges of the F(ab'), fragments. Alternatively, Fab expression libraries may be constructed (Huse et al., 1989, Science, 246: 1275-1281) to allow rapid and easy identification of monoclonal Fab fragments with the desired specificity.

Example 5

In a diagnostic screening example, Applicants' discovery is used to screen individuals to determine whether said individual carries the SARS-CoV or a non-SARS strain of coronavirus. In this example, the in vivo characteristic to be identified is a whether the strain of virus harbored by an individual is one that possesses ORF3, or alternatively and preferably, ORF3a.

In this example, a swab or a lavage of an individual's respiratory tract can be performed and the recovered virus lysed and viral genome extracted. Because coronaviruses, including SARS-CoV are RNA viruses, the extracted genome is subjected to reverse transcription PCR. Following reverse transcription, the cDNA is amplified using sense and antisense primers specific for a region of ORF3, and the amplified cDNA resolved on an agarose gel visualized with ethidium bromide.

Samples that produce an amplified product are those that have the ORF3, and in turn have ORF3 in their genome. Sample that produce no amplified virus are lacking ORF3. Such a diagnostic screen is useful for rapidly determining whether an individual is a carrier of SARS-CoV, and allows for proper treatment and care of individuals depending on the strain of coronavirus they are carrying.

Example 6

In a second diagnostic screening assay, virus recovered from an individual is genotyped to determine whether an individual carries the SARS-CoV. Thus, in this example, the in vivo characteristic to be identified is the coronavirus genotype, particularly the ORF3, and more particularly ORF3a.

In one example of this screening assay, the virus can be isolated and genomic RNA was extracted and reverse transcription PCR amplified as described in Example 5, above. The purified PCR product is sequenced using an automated sequencer, such as the ABI Prism 3100; however, any other sequencing procedure will reach the same result.

Samples that have the ORF3 sequence have a nucleotide sequence similar to that unique to SARS-CoV. Such a diagnostic screen is useful for rapidly determining whether an individual is a carrier of SARS-CoV, and allows for proper treatment and care of individuals depending on the strain of coronavirus they are carrying.

Various modifications and alterations of the invention will become apparent to those skilled in the art without departing from the spirit and scope of the invention, which is defined by the accompanying claims. For example, it should be noted that steps recited in any method claims below do not necessarily need to be performed in the order that they are recited. Those of ordinary skill in the art will recognize variations in performing the steps from the order in which they are recited. For example, in certain embodiments, steps may be performed simultaneously. The accompanying claims should be constructed with these principles in mind.

SEQUENCE LISTING

```
<160> NUMBER OF SEQ ID NOS: 21

<210> SEQ ID NO 1
<211> LENGTH: 274
<212> TYPE: PRT
<213> ORGANISM: Coronaviridae ORF3a encoded cAMP dep. kinase
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1

Met Asp Leu Phe Met Arg Phe Phe Thr Leu Xaa Ser Ile Thr Ala Gln
1               5                   10                  15

Pro Val Lys Ile Asp Asn Ala Ser Pro Ala Ser Thr Val His Ala Thr
            20                  25                  30

Ala Thr Ile Pro Leu Gln Ala Ser Leu Pro Phe Gly Trp Leu Val Ile
        35                  40                  45

Gly Val Ala Phe Leu Ala Val Phe Gln Ser Ala Thr Lys Ile Ile Ala
    50                  55                  60

Leu Asn Lys Arg Trp Gln Leu Ala Leu Tyr Lys Gly Phe Gln Phe Ile
65                  70                  75                  80

Cys Asn Leu Leu Leu Leu Phe Val Thr Ile Tyr Ser His Leu Leu Leu
                85                  90                  95

Val Ala Ala Gly Met Glu Ala Gln Phe Leu Tyr Leu Tyr Ala Leu Ile
            100                 105                 110

Tyr Phe Leu Gln Cys Ile Asn Ala Cys Arg Ile Ile Met Arg Cys Trp
        115                 120                 125

Leu Cys Trp Lys Cys Lys Ser Lys Asn Pro Leu Leu Tyr Asp Ala Asn
    130                 135                 140

Tyr Phe Val Cys Trp His Thr His Asn Tyr Asp Tyr Cys Ile Pro Tyr
145                 150                 155                 160

Asn Ser Val Thr Asp Thr Ile Val Val Thr Glu Gly Asp Gly Ile Ser
                165                 170                 175

Thr Pro Lys Leu Lys Glu Asp Tyr Gln Ile Gly Gly Tyr Ser Glu Asp
            180                 185                 190

Arg His Ser Gly Val Lys Asp Tyr Val Val Val His Gly Tyr Phe Thr
        195                 200                 205

Glu Val Tyr Tyr Gln Leu Glu Ser Thr Gln Ile Thr Thr Asp Thr Gly
    210                 215                 220

Ile Glu Asn Ala Thr Phe Phe Ile Phe Asn Lys Leu Val Lys Asp Pro
225                 230                 235                 240

Pro Asn Val Gln Ile His Thr Ile Asp Gly Ser Ser Gly Val Ala Asn
                245                 250                 255

Pro Ala Met Asp Pro Ile Tyr Asp Glu Pro Thr Thr Thr Thr Ser Val
            260                 265                 270

Pro Leu
```

<210> SEQ ID NO 2
<211> LENGTH: 154
<212> TYPE: PRT
<213> ORGANISM: Coronaviridae ORF3b kinase-associated C2 domain

<400> SEQUENCE: 2

Met Met Pro Thr Thr Leu Phe Ala Gly Thr His Ile Thr Met Thr Thr
1               5                   10                  15

Val Tyr His Ile Thr Val Ser Gln Ile Gln Leu Ser Leu Leu Lys Val
            20                  25                  30

Thr Ala Phe Gln His Gln Asn Ser Lys Lys Thr Lys Leu Val Val
        35                  40                  45

Ile Leu Arg Ile Gly Thr Gln Val Leu Lys Thr Met Ser Leu Tyr Met
    50                  55                  60

Ala Ile Ser Pro Lys Phe Thr Thr Ser Leu Ser Leu His Lys Leu Leu
65                  70                  75                  80

Gln Thr Leu Val Leu Lys Met Leu His Ser Ser Leu Thr Ser Leu
                85                  90                  95

Leu Lys Thr His Arg Met Cys Lys Tyr Thr Gln Ser Thr Ala Leu Gln
            100                 105                 110

Glu Leu Leu Ile Gln Gln Trp Ile Gln Phe Met Met Ser Arg Arg Arg
        115                 120                 125

Leu Leu Ala Cys Leu Cys Lys His Lys Lys Val Ser Thr Asn Leu Cys
    130                 135                 140

Thr His Ser Phe Arg Lys Lys Gln Val Arg
145                 150

<210> SEQ ID NO 3
<211> LENGTH: 29751
<212> TYPE: DNA
<213> ORGANISM: Coronaviridae SARS TOR2 GenBank

<400> SEQUENCE: 3

```
atattaggtt tttacctacc caggaaaagc caaccaacct cgatctcttg tagatctgtt    60
ctctaaacga actttaaaat ctgtgtagct gtcgctcggc tgcatgccta gtgcacctac   120
gcagtataaa caataataaa ttttactgtc gttgacaaga acgagtaac tcgtccctct    180
tctgcagact gcttacggtt cgtccgtgt tgcagtcgat catcagcata cctaggtttc    240
gtccgggtgt gaccgaaagg taagatggag agccttgttc ttggtgtcaa cgagaaaaca   300
cacgtccaac tcagtttgcc tgtccttcag gttagagacg tgctagtgcg tggcttcggg   360
gactctgtgg aagaggccct atcggaggca cgtgaacacc tcaaaaatgg cacttgtggt   420
ctagtagagc tggaaaaagg cgtactgccc cagcttgaac agccctatgt gttcattaaa   480
cgttctgatg ccttaagcac caatcacggc acaaggtcg ttgagctggt tgcagaaatg   540
gacggcattc agtacggtcg tagcggtata acactgggag tactcgtgcc acatgtgggc   600
gaaaccccaa ttgcataccg caatgttctt cttcgtaaga acggtaataa gggagccggt   660
ggtcatagct atggcatcga tctaaagtct tatgacttag gtgacgagct tggcactgat   720
cccattgaag attatgaaca aaactggaac actaagcatg gcagtggtgc actccgtgaa   780
ctcactcgtg agctcaatgg aggtgcagtc actcgctatg tcgacaacaa tttctgtggc   840
ccagatgggt accctcttga ttgcatcaaa gattttctcg cacgcgcggg caagtcaatg   900
tgcactcttt ccgaacaact tgattacatc gagtcgaaga gaggtgtcta ctgctgccgt   960
gaccatgagc atgaaattgc ctggttcact gagcgctctg ataagagcta cgagcaccag  1020
```

```
acacccttcg aaattaagag tgccaagaaa tttgacactt tcaaggggga atgcccaaag    1080
tttgtgtttc ctcttaactc aaaagtcaaa gtcattcaac cacgtgttga aaagaaaaag    1140 actgaggggtt tcatggggcg tatacgctct gtgtaccctg ttgcatctcc acaggagtgt   1200
aacaatatgc acttgtctac cttgatgaaa tgtaatcatt gcgatgaagt ttcatggcag    1260
acgtgcgact ttctgaaagc cacttgtgaa cattgtggca ctgaaaattt agttattgaa    1320
ggacctacta catgtgggta cctacctact aatgctgtag tgaaaatgcc atgtcctgcc    1380
tgtcaagacc cagagattgg acctgagcat agtgttgcag attatcacaa ccactcaaac    1440
attgaaactc gactccgcaa gggaggtagg actagatgtt ttggaggctg tgtgtttgcc    1500
tatgttggct gctataataa gcgtgcctac tgggttcctc gtgctagtgc tgatattggc    1560
tcaggccata ctggcattac tggtgacaat gtggagacct gaatgagga tctccttgag    1620 atactgagtc gtgaacgtgt taacattaac attgttggcg attttcattt gaatgaagag    1680
gttgccatca ttttggcatc tttctctgct tctacaagtg cctttattga cactataaag    1740
agtcttgatt acaagtcttt caaaaccatt gttgagtcct gcggtaacta taaagttacc    1800
aagggaaagc ccgtaaaagg tgcttggaac attggacaac agagatcagt tttaacacca    1860
ctgtgtggtt ttccctcaca ggctgctggt gttatcagat caattttttgc gcgcacactt    1920 gatgcagcaa accactcaat tcctgatttg caaagagcag ctgtcaccat acttgatggt    1980
atttctgaac agtcattacg tcttgtcgac gccatggttt atacttcaga cctgctcacc    2040
aacagtgtca ttattatggc atatgtaact ggtggtcttg tacaacagac ttctcagtgg    2100
ttgtctaatc tttttgggcac tactgttgaa aaactcaggc ctatctttga atggattgag    2160
gcgaaactta gtgcaggagt tgaatttctc aaggatgctt gggagattct caaatttctc    2220
attacaggtg ttttttgacat cgtcaagggt caaatacagg ttgcttcaga taacatcaag    2280
gattgtgtaa aatgcttcat tgatgttgtt aacaaggcac tcgaaatgtg cattgatcaa    2340
gtcactatcg ctggcgcaaa gttgcgatca ctcaacttag gtgaagtctt catcgctcaa    2400
agcaagggac tttaccgtca gtgtatacgt ggcaaggagc agctgcaact actcatgcct    2460
cttaaggcac caaaagaagt aacctttctt gaaggtgatt cacatgacac agtacttacc    2520
tctgaggagg ttgttctcaa gaacggtgaa ctcgaagcac tcgagacgcc cgttgatagc    2580
ttcacaaatg gagctatcgt tggcacacca gtctgtgtaa atggcctcat gctcttagag    2640
attaaggaca agaacaata ctgcgcattg tctcctggtt tactggctac aaacaatgtc    2700
tttcgcttaa aggggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa acttttcatc acgtatgtat tgttccttttt acccctccaga tgaggaagaa    3060 gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg gatgatgacta ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
```

```
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540
ctgcatgttg ttggacctaa cctaaatgca ggtgaggaca tccagcttct taaggcagca   3600
tatgaaaatt tcaattcaca ggacatctta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag agccaccaa acacagaaga ttccaaaact    3840
gaggagaaat ctgtcgtaca gaagcctgtc gatgtgaagc caaaaattaa ggcctgcatt   3900
gatgaggtta ccacaacact ggaagaaact aagtttctta ccaataagtt actcttgttt   3960
gctgatatca atggtaagct ttaccatgat tctcagaaca tgcttagagg tgaagatatg   4020
tctttccttg agaaggatgc accttacatg gtaggtgatg ttatcactag tggtgatatc   4080
acttgtgttg taatacccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctaa gactgctctt aagaaatgca atctgcatt ttatgtacta    4260 ccttcagaag cacctaatgc taaggaagag attctaggaa ctgtatcctg gaatttgaga   4320
gaaatgcttg ctcatgctga agagacaaga aaattaatgc ctatatgcat ggatgttaga   4380
gccataatgg caaccatcca acgtaagtat aaaggaatta aaattcaaga gggcatcgtt   4440
gactatggtg tccgattctt cttttatact agtaaagagc ctgtagcttc tattattacg   4500
aagctgaact ctctaaatga ccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca   4680
tctgaggagc acttttgtaga aacagtttct ttggctggct cttacagaga ttggtcctat   4740
tcaggacagc gtacagagtt aggtgttgaa tttcttaagc gtggtgacaa aattgtgtac   4800
cacactctgg agagccccgt cgagtttcat cttgacggtg aggttctttc acttgacaaa   4860
ctaaagagtc tcttatccct gcgggaggtt aagactataa agtgttcac aactgtggac    4920 aacactaatc tccacacaca gcttgtggat atgtctatga catatggaca gcagtttggt   4980
ccaacatact ggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta cttttgtgc actcatactc   5340 gcttacagta ataaaactgt tggcgagctt ggtgatgtca gagaaactat gacccatctt   5400
ctacagcatg ctaatttgga atctgcaaag cgagttctta atgtggtgtg taaacattgt   5460
ggtcagaaaa ctactaccctt aacgggtgta gaagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtcattctt atgtgcgaat gagtacactg gtaactatca gtgtggtcat   5700
tacactcata taactgctaa ggagacccctc tatcgtattg acggagctca ccttacaaag   5760
```

```
atgtcagagt acaaaggacc agtgactgat gttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga agtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
atggctgctt atgtggaaaa cacaagcatt accattaaga aacctaatga gctttcacta    6540
gccttaggtt taaaaacaat tgccactcat ggtattgctg caattaatag tgttccttgg    6600
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt ggcatatat gttgttcaca    7200
aaattctttt atttattagg tctttcagct ataatgcagg tgttctttgg ctattttgct    7260
agtcatttca tcagcaattc ttggctcatg tggtttatca ttagtattgt acaaatggca    7320
cccgttctg caatggttag gatgtacatc ttctttgctt cttttctacta catatggaag    7380
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg gcgcgcttca cctctacttt gacaaggctg gtcaaaagac ctatgagaga    7740
catccgctct cccatttttgt caatttagac aatttgagag ctaacaacac taaaggttca    7800
ctgcctatta atgtcatagt ttttgatggc aagtccaaat gcgacgagtc tgcttctaag    7860
tctgcttctg tgtactacag tcagctgatg tgccaaccta ttctgttgct tgaccaagct    7920
cttgtatcag acgttggaga tagtactgaa gtttccgtta agatgtttga tgcttatgtc    7980
gacaccttt cagcaacttt tagtgttcct atggaaaaac ttaaggcact tgttgctaca    8040
gctcacagcg agttagcaaa gggtgtagct ttagatggtg tcctttctac attcgtgtca    8100
```

```
gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtctttatc tgaacagctg cgtaaacaaa ttcgtagtgc tgccaagaag    8400
aacaacatac cttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtacataca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta caagagagat tggtttcata gtgcctggct taccgggtac tgtgctgaga    8820
gcaatcaatg gtgacttctt gcattttcta cctcgtgttt ttagtgctgt tggcaacatt    8880
tgctacacac cttccaaact cattgagtat agtgattttg ctacctctgc ttgcgttctt    8940
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt tgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgttttggg tgagtacaac    9420
catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgccttttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac ctttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaagggt gcatggtaca agtaacctgt ggaactacaa ctcttaatgg attgtggttg    10080
gatgacacag tatactgtcc aagacatgtc atttgcacag cagaagacat gcttaatcct    10140
aactatgaag atctgctcat tcgcaaatcc aaccatagct tcttgttca ggctggcaat    10200 gttcaacttc gtgttattgg ccattctatg caaaattgtc tgcttaggct taagttgat    10260 acttctaacc ctaagacacc caagtataaa tttgtccgta tccaacctgg tcaaacatttt   10320 tcagttctag catgctacaa tggttcacca tctggtgttt atcagtgtgc catgagacct    10380
aatcatacca ttaaaggttc tttccttaat ggatcatgtg gtagtgttgg ttttaacatt    10440
gattatgatt gcgtgtcttt ctgctatatg catcatatgg agcttccaac aggagtacac    10500
```

```
gctggtactg acttagaagg taaattctat ggtccatttg ttgacagaca aactgcacag   10560
gctgcaggta cagacacaac cataacatta aatgttttgg catggctgta tgctgctgtt   10620
atcaatggtg ataggtggtt tcttaataga ttcaccacta ctttgaatga ctttaacctt   10680
gtggcaatga agtacaacta tgaacctttg acacaagatc atgttgacat attgggacct   10740
ctttctgctc aaacaggaat tgccgtctta gatatgtgtg ctgctttgaa agagctgctg   10800
cagaatggta tgaatggtcg tactatcctt ggtagcacta ttttagaaga tgagtttaca   10860
ccatttgatg ttgttagaca atgctctggt gttaccttcc aaggtaagtt caagaaaatt   10920
gttaagggca ctcatcattg gatgctttta actttcttga catcactatt gattcttgtt   10980
caaagtacac agtggtcact gttttttcttt gtttacgaga atgctttctt gccatttact   11040
cttggtatta tggcaattgc tgcatgtgct atgctgcttg ttaagcataa gcacgcattc   11100
ttgtgcttgt ttctgttacc ttctcttgca acagttgctt actttaatat ggtctacatg   11160
cctgctagct gggtgatgcg tatcatgaca tggcttgaat tggctgacac tagcttgtct   11220
ggttataggc ttaaggattg tgttatgtat gcttcagctt tagttttgct tattctcatg   11280
acagctcgca ctgtttatga tgatgctgct agacgtgttt ggacactgat gaatgtcatt   11340
acacttgttt acaaagtcta ctatggtaat gctttagatc aagctatttc catgtgggcc   11400
ttagttattt ctgtaacctc taactattct ggtgtcgtta cgactatcat gttttagct    11460 agagctatag tgtttgtgtg tgttgagtat tacccattgt tatttattac tggcaacacc   11520
ttacagtgta tcatgcttgt ttattgtttc ttaggctatt gttgctgctg ctactttggc   11580
cttttctgtt tactcaaccg ttacttcagg cttactcttg gtgtttatga ctacttggtc   11640
tctacacaag aatttaggta tatgaactcc caggggcttt tgcctcctaa gagtagtatt   11700
gatgctttca gcttaacat taagttgttg ggtattggag gtaaaccatg tatcaaggtt   11760
gctactgtac agtctaaaat gtctgacgta aagtgcacat ctgtggtact gctctcggtt   11820
cttcaacaac ttagagtaga gtcatcttct aaattgtggg cacaatgtgt acaactccac   11880
aatgatattc ttcttgcaaa agacacaact gaagctttcg agaagatggt ttctcttttg   11940
tctgttttgc tatccatgca gggtgctgta gacattaata ggttgtgcga ggaaatgctc   12000
gataaccgtg ctactcttca ggctattgct tcagaattta gttctttacc atcatatgcc   12060
gcttatgcca ctgcccagga ggcctatgag caggctgtag ctaatggtga ttctgaagtc   12120
gttctcaaaa agtaaagaa atctttgaat gtggctaaat ctgagtttga ccgtgatgct   12180
gccatgcaac gcaagttgga aaagatggca gatcaggcta tgacccaaat gtacaaacag   12240
gcaagatctg aggacaagag ggcaaaagta actagtgcta tgcaaacaat gctcttcact   12300
atgcttagga agcttgataa tgatgcactt aacaacatta tcaacaatgc gcgtgatggt   12360
tgtgttccac tcaacatcat accattgact acagcagcca aactcatggt tgttgtccct   12420
gattatggta cctacaagaa cacttgtgat ggtaacacct ttacatatgc atctgcactc   12480
tgggaaatcc agcaagttgt tgatgcggat agcaagattg ttcaacttag tgaaattaac   12540
atggacaatt caccaaattt ggcttggcct cttattgtta cagctctaag agccaactca   12600
gctgttaaac tacagaataa tgaactgagt ccagtagcac tacgacagat gtcctgtgcg   12660
gctggtacca cacaaacagc ttgtactgat gacaatgcac ttgcctacta taacaattcg   12720
aagggaggta ggtttgtgct ggcattacta tcagaccacc aagatctcaa atgggctaga   12780
ttccctaaga gtgatggtac aggtacaatt tacacagaac tggaaccacc ttgtaggttt   12840
```

```
gttacagaca caccaaaagg gcctaaagtg aaatacttgt acttcatcaa aggcttaaac   12900
aacctaaata gaggtatggt gctgggcagt ttagctgcta cagtacgtct tcaggctgga   12960
aatgctacag aagtacctgc caattcaact gtgctttcct tctgtgcttt tgcagtagac   13020
cctgctaaag catataagga ttacctagca agtggaggac aaccaatcac caactgtgtg   13080
aagatgttgt gtacacacac tggtacagga caggcaatta ctgtaacacc agaagctaac   13140
atggaccaag agtcctttgg tggtgcttca tgttgtctgt attgtagatg ccacattgac   13200
catccaaatc ctaaaggatt ctgtgacttg aaaggtaagt acgtccaaat acctaccact   13260
tgtgctaatg acccagtggg ttttacactt agaaacacag tctgtaccgt ctgcggaatg   13320
tggaaaggtt atggctgtag ttgtgaccaa ctccgcgaac ccttgatgca gtctgcggat   13380
gcatcaacgt ttttaaacgg gtttgcggtg taagtgcagc ccgtcttaca ccgtgcggca   13440
caggcactag tactgatgtc gtctacaggg cttttgatat ttacaacgaa aaagttgctg   13500
gttttgcaaa gttcctaaaa actaattgct gtcgcttcca ggagaaggat gaggaaggca   13560
atttattaga ctcttacttt gtagttaaga ggcatactat gtctaactac caacatgaag   13620
agactattta aacttggtt aaagattgtc cagcggttgc tgtccatgac ttttcaagt     13680 ttagagtaga tggtgacatg gtaccacata tatcacgtca gcgtctaact aaatacacaa   13740
tggctgattt agtctatgct ctacgtcatt ttgatgaggg taattgtgat acattaaaag   13800
aaatactcgt cacatacaat gctgtgatg atgattattt caataagaag gattggtatg    13860
acttcgtaga gaatcctgac atcttacgcg tatatgctaa cttaggtgag cgtgtacgcc   13920
aatcattatt aaagactgta caattctgcg atgctatgcg tgatgcaggc attgtaggcg   13980
tactgacatt agataatcag gatcttaatg ggaactggta cgatttcggt gatttcgtac   14040
aagtagcacc aggctgcgga gttcctattg tggattcata ttactcattg ctgatgccca   14100
tcctcacttt gactagggca ttggctgctg agtcccatat ggatgctgat ctcgcaaaac   14160
cacttattaa gtgggatttg ctgaaatatg attttacgga agagagactt tgtctcttcg   14220
accgttattt taaatattgg gaccagacat accatcccaa ttgtattaac tgtttggatg   14280
ataggtgtat ccttcattgt gcaaacttta atgtgttatt ttctactgtg tttccaccta   14340
caagttttgg accactagta agaaaaatat ttgtagatgg tgttcctttt gttgtttcaa   14400
ctggatacca ttttcgtgag ttaggagtcg tacataatca ggatgtaaac ttacatagct   14460
cgcgtctcag tttcaaggaa cttttagtgt atgctgctga tccagctatg catgcagctt   14520
ctggcaattt attgctagat aaacgcacta catgcttttc agtagctgca ctaacaaaca   14580
atgttgcttt tcaaactgtc aaacccggta attttaataa agacttttat gactttgctg   14640
tgtctaaagg ttttcttaag gaaggaagtt ctgttgaact aaaacacttc ttctttgctc   14700
aggatggcaa cgctgctatc agtgattatg actattatcg ttataatctg ccaacaatgt   14760
gtgatatcag acaactccta ttcgtagttg aagttgttga taaatacttt gattgttacg   14820
atggtggctg tattaatgcc aaccaagtaa tcgttaacaa tctggataaa tcagctggtt   14880
tcccatttaa taaatggggt aaggctagac tttattatga ctcaatgagt tatgaggatc   14940
aagatgcact tttcgcgtat actaagcgta atgtcatccc tactataact caaatgaatc   15000
ttaagtatgc cattagtgca aagaatagag ctcgcaccgt agctggtgtc tctatctgta   15060
gtactatgac aaatagacag tttcatcaga aattattgaa gtcaatagcc gccactagag   15120
gagctactgt ggtaattgga acaagcaagt tttacggtgg ctggcataat atgttaaaaa   15180
ctgtttacag tgatgtagaa actccacacc ttatggggttg ggattatcca aaatgtgaca   15240
```

```
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccaatg    15480
taaatgcact tcttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720 cagttctttta ttatcaaaat aatgtgttca tgtctgaggc aaaatgttgg actgagactg    15780
accttactaa aggacctcac gaattttgct cacagcatac aatgctagtt aaacaaggag    15840
atgattacgt gtacctgcct tacccagatc catcaagaat attaggcgca ggctgttttg    15900
tcgatgatat tgtcaaaaca gatggtacac ttatgattga aggttcgtg tcactggcta    15960 ttgatgctta cccacttaca aaacatccta atcaggagta tgctgatgtc tttcacttgt    16020
atttacaata cattagaaag ttacatgatg agcttactgg ccacatgttg gacatgtatt    16080
ccgtaatgct aactaatgat aacacctcac ggtactggga acctgagttt tatgaggcta    16140
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatcccat gtttgcaatg    16320 ccccaggttg tgatgtcact gatgtgcaca actgtatct aggaggtatg agctattatt    16380
gcaagtcaca taagcctccc attagtttc cattatgtgc taatggtcag gttttggtt    16440 tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ccactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac accttttgaaa aaggtgacta tggtgatgct gttgtgtaca    16800
gaggtactac gacatacaag ttgaatgttg gtgattactt tgttttgaca tctcacactg    16860
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcatttg    17040 ccatcggact tgctctctat acccatctg ctcgcatagt gtatacggca tgctctcatg    17100
cagctgttga tgcccctatgt gaaaaggcat taaaatattt gcccatagat aaatgtagta    17160
gaatcatacc tgcgcgtgcg cgcgtagagt gttttgataa attcaaagtg aattcaacac    17220
tagaacagta tgtttttctgc actgtaaatg cattgccaga acaactgct gacattgtag    17280 tctttgatga aatctctatg gctactaatt atgacttgag tgttgtcaat gctagacttc    17340
gtgcaaaaca ctacgtctat attggcgatc ctgctcaatt accagcccc cgcacattgc    17400 tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
```

```
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700 tctcaccta  taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaaatgt aactggactt tttaaggact    18000
gtagtaagat cattactggt cttcatccta cacaggcacc tacacacctc agcgttgata    18060
taaagttcaa gactgaagga ttatgtgttg ataccagg   cataccaaag gacatgacct    18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga agaacgtgt  tgtctgtgtg    18600 acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaataccct attataggag atgaactgag ggttaattct gcttgcagaa    18900
aagtacaaca catggttgtg aagtctgcat tgcttgctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggaactcttc tattcttatg    19080
ctacacatca cgataaattc actgatggtg tttgttgtt ttggaattgt aacgttgatc    19140
gttacccagc caatgcaatt gtgtgtaggt ttgacacaag agtcttgtca aacttgaact    19200
taccaggctg tgatggtggt agtttgtatg tgaataagca tgcattccac actccagctt    19260
tcgataaaag tgcatttact aatttaaagc aattgccttt cttttactat tctgatagtc    19320
cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta aatgttgtt  aataaaggac actttgatgg acacgccggc gaagcacctg    19620
tttccatcat taataatgct gtttacacaa aggtagatgg tattgatgtg agatctttg    19680 aaaataagac aacacttcct gttaatgttg catttgagct ttgggctaag cgtaacatta    19740
aaccagtgcc agagattaag atactcaata atttgggtgt tgatatcgct gctaatactg    19800
taatctggga ctacaaaaga gaagccccag cacatgtatc tacaataggt gtctgcacaa    19860
tgactgacat tgccaagaaa cctactgaga gtgcttgttc ttcacttact gtcttgtttg    19920
atggtagagt ggaaggacag gtagaccttt ttagaaacgc ccgtaatggt gtttttaataa    19980
```

```
cagaaggttc agtcaaaggt ctaacacctt caaagggacc agcacaagct agcgtcaatg   20040
gagtcacatt aattggagaa tcagtaaaaa cacagtttaa ctactttaag aaagtagacg   20100
gcattattca acagttgcct gaaacctact ttactcagag cagagactta gaggatttta   20160
agcccagatc acaaatggaa actgactttc tcgagctcgc tatggatgaa ttcatacagc   20220
gatataagct cgagggctat gccttcgaac acatcgttta tggagatttc agtcatggac   20280
aacttggcgg tcttcattta atgataggct tagccaagcg ctcacaagat tcaccactta   20340
aattagagga ttttatccct atggacagca cagtgaaaaa ttacttcata acagatgcgc   20400
aaacaggttc atcaaaatgt gtgtgttctg tgattgatct tttacttgat gactttgtcg   20460
agataataaa gtcacaagat ttgtcagtga tttcaaaagt ggtcaaggtt acaattgact   20520
atgctgaaat ttcattcatg ctttggtgta aggatggaca tgttgaaacc ttctacccaa   20580
aactacaagc aagtcaagcg tggcaaccag gtgttgcgat gcctaacttg tacaagatgc   20640
aaagaatgct tcttgaaaag tgtgaccttc agaattatgg tgaaaatgct gttataccaa   20700
aaggaataat gatgaatgtc gcaaagtata ctcaactgtg tcaatactta aatcacttta   20760
ctttagctgt accctacaac atgagagtta ttcactttgg tgctggctct gataaaggag   20820
ttgcaccagg tacagctgtg ctcagacaat ggttgccaac tggcacacta cttgtcgatt   20880
cagatcttaa tgacttcgtc tccgacgcag attctacttt aattggagac tgtgcaacag   20940
tacatacggc taataaatgg gaccttatta ttagcgatat gtatgaccct aggaccaaac   21000
atgtgacaaa agagaatgac tctaaagaag gttttttcac ttatctgtgt ggatttataa   21060
agcaaaaact agccctgggt ggttctatag ctgtaaagat aacagagcat tcttggaatg   21120 ctgacctta caagcttatg ggccatttct catggtggac agcttttgtt acaaatgtaa   21180
atgcatcatc atcggaagca ttttaattg gggctaacta tcttggcaag ccgaaggaac   21240
aaattgatgg ctataccatg catgctaact acatttctg gaggaacaca aatcctatcc   21300
agttgtcttc ctattcactc tttgacatga gcaaatttcc tcttaaatta agaggaactg   21360
ctgtaatgtc tcttaaggag aatcaaatca atgatatgat ttattctctt ctggaaaaag   21420
gtaggcttat cattagagaa acaacagag ttgtggtttc aagtgatatt cttgttaaca   21480
actaaacgaa catgtttatt ttcttattat ttcttactct cactagtggt agtgaccttg   21540
accggtgcac cacttttgat gatgttcaag ctcctaatta cactcaacat acttcatcta   21600
tgaggggggt ttactatcct gatgaaattt ttagatcaga cactcttttat ttaactcagg   21660 atttatttct tccattttat tctaatgtta cagggtttca tactattaat catacgtttg   21720
gcaaccctgt cataccttt aaggatggta tttattttgc tgccacagag aaatcaaatg   21780
ttgtccgtgg ttgggttttt ggttctacca tgaacaacaa gtcacagtcg gtgattatta   21840
ttaacaattc tactaatgtt gttatacgag catgtaactt tgaattgtgt gacaacccttt   21900 tctttgctgt ttctaaaccc atgggtacac agacacatac tatgatattc gataatgcat   21960
ttaattgcac tttcgagtac atatctgatg ccttttcgct tgatgtttca gaaaagtcag   22020
gtaattttaa acacttacga gagtttgtgt ttaaaaataa agatgggttt ctctatgttt   22080
ataagggcta tcaacctata gatgtagttc gtgatctacc ttctggtttt aacactttga   22140
aacctatttt taagttgcct cttggtatta acattacaaa ttttagagcc attcttacag   22200
ccttttcacc tgctcaagac atttgggca cgtcagctgc agcctatttt gttggctatt   22260
taaagccaac tacatttatg ctcaagtatg atgaaaatgg tacaatcaca gatgctgttg   22320
```

```
attgttctca aaatccactt gctgaactca aatgctctgt taagagcttt gagattgaca  22380
aaggaattta ccagacctct aatttcaggg ttgttccctc aggagatgtt gtgagattcc  22440
ctaatattac aaacttgtgt cctttggag aggtttttaa tgctactaaa ttcccttctg   22500
tctatgcatg ggagagaaaa aaaatttcta attgtgttgc tgattactct gtgctctaca  22560
actcaacatt tttttcaacc tttaagtgct atggcgtttc tgccactaag ttgaatgatc  22620
tttgcttctc caatgtctat gcagattctt ttgtagtcaa gggagatgat gtaagacaaa  22680
tagcgccagg acaaactggt gttattgctg attataatta taaattgcca gatgatttca  22740
tgggttgtgt ccttgcttgg aatactagga acattgatgc tacttcaact ggtaattata  22800
attataaata taggtatctt agacatggca agcttaggcc ctttgagaga gacatatcta  22860
atgtgccttt ctcccctgat ggcaaacctt gcaccccacc tgctcttaat tgttattggc  22920
cattaaatga ttatggtttt tacaccacta ctggcattgg ctaccaacct tacagagttg  22980
tagtactttc ttttgaactt ttaaatgcac cggccacggt ttgtggacca aaattatcca  23040
ctgaccttat taagaaccag tgtgtcaatt ttaattttaa tggactcact ggtactggtg  23100
tgttaactcc ttcttcaaag agatttcaac catttcaaca atttggccgt gatgtttctg  23160
atttcactga ttccgttcga gatcctaaaa catctgaaat attagacatt tcaccttgcg  23220
cttttgggg tgtaagtgta attacacctg gaacaaatgc ttcatctgaa gttgctgttc  23280
tatatcaaga tgttaactgc actgatgttt ctacagcaat tcatgcagat caactcacac  23340
cagcttggcg catatattct actggaaaca atgtattcca gactcaagca ggctgtctta  23400
taggagctga gcatgtcgac acttcttatg agtgcgacat tcctattgga gctggcattt  23460
gtgctagtta ccatacagtt tctttattac gtagtactag ccaaaaatct attgtggctt  23520
atactatgtc tttaggtgct gatagttcaa ttgcttactc taataacacc attgctatac  23580
ctactaactt ttcaattagc attactacag aagtaatgcc tgtttctatg ctaaaaacct  23640
ccgtagattg taatatgtac atctgcggag attctactga atgtgctaat ttgcttctcc  23700
aatatggtag cttttgcaca caactaaatc gtgcactctc aggtattgct gctgaacagg  23760
atcgcaacac acgtgaagtg ttcgctcaag tcaaacaaat gtacaaaacc ccaactttga  23820
aatatttggg tggttttaat ttttcacaaa tattacctga ccctctaaag ccaactaaga  23880
ggtcttttat tgaggacttg ctctttaata aggtgacact cgctgatgct ggcttcatga  23940
agcaatatgg cgaatgccta ggtgatatta tgctagaga tctcatttgt gcgcagaagt  24000
tcaatggact tacagtgttg ccacctctgc tcactgatga tatgattgct gcctacactg  24060
ctgctctagt tagtggtact gccactgctg gatggacatt tggtgctggc gctgctcttc  24120
aaataccttt tgctatgcaa atggcatata ggttcaatgg cattggagtt acccaaaatg  24180
ttctctatga gaaccaaaaa caaatcgcca accaatttaa caggcgatt agtcaaattc    24240
aagaatcact tacaacaaca tcaactgcat tgggcaagct gcaagacgtt gttaaccaga  24300
atgctcaagc attaaacaca cttgttaaac aacttagctc taattttggt gcaatttcaa  24360
gtgtgctaaa tgatatcctt tcgcgacttg ataaagtcga ggcggaggta caaattgaca  24420
ggttaattac aggcagactt caaagccttc aaacctatgt aacacaacaa ctaatcaggg  24480
ctgctgaaat cagggcttct gctaatcttg ctgctactaa aatgtctgag tgtgttcttg  24540
gacaatcaaa aagagttgac ttttgtggaa agggctacca ccttatgtcc ttcccacaag  24600
cagccccgca tggtgttgtc ttcctacatg tcacgtatgt gccatcccag gagaggaact  24660
tcaccacagc gccagcaatt tgtcatgaag gcaaagcata cttccctcgt gaaggtgttt  24720
```

```
ttgtgtttaa tggcacttct tggtttatta cacagaggaa cttcttttct ccacaaataa    24780
ttactacaga caatacattt gtctcaggaa attgtgatgt cgttattggc atcattaaca    24840
acacagttta tgatcctctg caacctgagc ttgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa aatatgagca atatattaaa tggccttggt    25080
atgtttggct cggcttcatt gctggactaa ttgccatcgt catggttaca atcttgcttt    25140
gttgcatgac tagttgttgc agttgcctca agggtgcatg ctcttgtggt tcttgctgca    25200
agtttgatga ggatgactct gagccagttc tcaagggtgt caaattacat tacacataaa    25260
cgaacttatg gatttgttta tgagattttt tactcttaga tcaattactg cacagccagt    25320
aaaaattgac aatgcttctc ctgcaagtac tgttcatgct acagcaacga taccgctaca    25380
agcctcactc cctttcggat ggcttgttat tggcgttgca tttcttgctg ttttttcagag   25440 cgctaccaaa ataattgcgc tcaataaaag atggcagcta gcccctttata agggcttcca    25500 gttcatttgc aatttactgc tgctatttgt taccatctat tcacatcttt tgcttgtcgc    25560
tgcaggtatg gaggcgcaat ttttgtacct ctatgccttg atatattttc tacaatgcat    25620
caacgcatgt agaattatta tgagatgttg gctttgttgg aagtgcaaat ccaagaaccc    25680
attactttat gatgccaact actttgtttg ctggcacaca cataactatg actactgtat    25740
accatataac agtgtcacag atacaattgt cgttactgaa ggtgacggca tttcaacacc    25800
aaaactcaaa gaagactacc aaattggtgg ttattctgag gataggcact caggtgttaa    25860
agactatgtc gttgtacatg gctatttcac cgaagtttac taccagcttg agtctacaca    25920
aattactaca gacactggta ttgaaaatgc tacattcttc atctttaaca agcttgttaa    25980 agaccccaccg aatgtgcaaa tacacacaat cgacggctct tcaggagttg ctaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt ctttttcttg ctttcgtggt attcttgcta gtcacactag ccatccttac    26220
tgcgcttcga ttgtgtgcgt actgctgcaa tattgttaac gtgagtttag taaaaccaac    26280
ggtttacgtc tactcgcgtg ttaaaaatct gaactcttct gaaggagttc ctgatcttct    26340
ggtctaaacg aactaactat tattattatt ctgtttggaa ctttaacatt gcttatcatg    26400
gcagacaacg gtactattac cgttgaggag cttaaacaac tcctggaaca atggaaccta    26460
gtaataggtt tcctattcct agcctggatt atgttactac aatttgccta ttctaatcgg    26520
aacaggtttt tgtacataat aaagcttgtt ttcctctggc tcttgtggcc agtaacactt    26580
gcttgttttg tgcttgctgc tgtctacaga attaattggg tgactggcgg gattgcgatt    26640
gcaatggctt gtattgtagg cttgatgtgg cttagctact tcgttgcttc cttcaggctg    26700
tttgctcgta cccgctcaat gtggtcattc aacccagaaa caaacattct tctcaatgtg    26760
cctctccggg ggacaattgt gaccagaccg ctcatggaaa gtgaacttgt cattggtgct    26820
gtgatcattc gtggtcactt gcgaatggcc ggacactccc tagggcgctg tgacattaag    26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
```

```
taagtgacaa cagatgtttc atcttgttga cttccaggtt acaatagcag agatattgat   27120
tatcattatg aggactttca ggattgctat ttggaatctt gacgttataa taagttcaat   27180
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcagac   27540
aagaggaggt tcaacaagag ctctactcgc cacttttttct cattgttgct gctctagtat   27600
ttttaatact ttgcttcacc attaagaaa agacagaatg aatgagctca ctttaattga   27660
cttctatttg tgcttttttag cctttctgct attccttgtt ttaataatgc ttattatatt   27720
ttggttttca ctcgaaatcc aggatctaga agaaccttgt accaaagtct aaacgaacat   27780
gaaacttctc attgttttga cttgtatttc tctatgcagt tgcatatgca ctgtagtaca   27840
gcgctgtgca tctaataaac ctcatgtgct tgaagatcct tgtaaggtac aacactaggg   27900
gtaatactta tagcactgct tggctttgtg ctctaggaaa ggttttacct tttcatagat   27960
ggcacactat ggttcaaaca tgcacaccta atgttactat caactgtcaa gatccagctg   28020
gtggtgcgct tatagctagg tgttggtacc ttcatgaagg tcaccaaact gctgcattta   28080
gagacgtact tgttgtttta aataaacgaa caaattaaaa tgtctgataa tggaccccaa   28140
tcaaaccaac gtagtgcccc ccgcattaca tttggtggac ccacagattc aactgacaat   28200
aaccagaatg gaggacgcaa tggggcaagg ccaaaacagc gccgacccca aggtttaccc   28260
aataatactg cgtcttggtt cacagctctc actcagcatg gcaaggagga acttagattc   28320
cctcgaggcc agggcgttcc aatcaacacc aatagtggtc cagatgacca aattggctac   28380
taccgaagag ctacccgacg agttcgtggt ggtgacggca aaatgaaaga gctcagcccc   28440
agatggtact tctattacct aggaactggc ccagaagctt cacttcccta cggcgctaac   28500
aaagaaggca tcgtatgggt tgcaactgag ggagccttga atacacccaa agaccacatt   28560
ggcacccgca atcctaataa caatgctgcc accgtgctac aacttcctca aggaacaaca   28620
ttgccaaaag gcttctacgc agagggaagc agaggcggca gtcaagcctc ttctcgctcc   28680
tcatcacgta gtcgcggtaa ttcaagaaat tcaactcctg gcagcagtag gggaaattct   28740
cctgctcgaa tggctagcgg aggtggtgaa actgccctcg cgctattgct gctagacaga   28800
ttgaaccagc ttgagagcaa agtttctggt aaaggccaac aacaacaagg ccaaactgtc   28860
actaagaaat ctgctgctga ggcatctaaa aagcctcgcc aaaaacgtac tgccacaaaa   28920
cagtacaacg tcactcaagc atttgggaga cgtggtccag aacaaaccca aggaaatttc   28980
ggggaccaag acctaatcag acaaggaact gattacaaac attggccgca aattgcacaa   29040
tttgctccaa gtgcctctgc attctttgga atgtcacgca ttggcatgga agtcacacct   29100
tcgggaacat ggctgactta tcatggagcc attaaattgg atgacaaaga tccacaattc   29160
aaagacaacg tcatactgct gaacaagcac attgacgcat acaaaacatt cccaccaaca   29220
gagcctaaaa aggacaaaaa gaaaagact gatgaagctc agcctttgcc gcagagacaa   29280
aagaagcagc ccactgtgac tcttcttcct gcggctgaca tggatgattt ctccagacaa   29340
cttcaaaatt ccatgagtgg agcttctgct gattcaactc aggcataaac actcatgatg   29400
accacacaag gcagatgggc tatgtaaacg ttttcgcaat tccgtttacg atacatagtc   29460
```

```
tactcttgtg cagaatgaat tctcgtaact aaacagcaca agtaggttta gttaacttta    29520
atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700
attttaatag cttcttagga gaatgacaaa aaaaaaaaa aaaaaaaaa a               29751

<210> SEQ ID NO 4
<211> LENGTH: 29751
<212> TYPE: DNA
<213> ORGANISM: Coronaviridae SARS TOR2 Release 3 from Canada's Michael
      Smith Genome Sciences Centre

<400> SEQUENCE: 4
atattaggtt tttacctacc caggaaaagc caaccaacct cgatctcttg tagatctgtt     60
ctctaaacga actttaaaat ctgtgtagct gtcgctcggc tgcatgccta gtgcacctac    120
gcagtataaa caataataaa ttttactgtc gttgacaaga aacgagtaac tcgtccctct    180
tctgcagact gcttacggtt tcgtccgtgt tgcagtcgat catcagcata cctaggtttc    240
gtccgggtgt gaccgaaagg taagatggag agccttgttc ttggtgtcaa cgagaaaaca    300
cacgtccaac tcagtttgcc tgtccttcag gttagacg tgctagtgcg tggcttcggg     360
gactctgtgg aagaggccct atcggaggca cgtgaacacc tcaaaaatgg cacttgtggt    420
ctagtagagc tggaaaaagg cgtactgccc cagcttgaac agccctatgt gttcattaaa    480
cgttctgatg ccttaagcac caatcacggc cacaaggtcg ttgagctggt tgcagaaatg    540
gacggcattc agtacggtcg tagcggtata acactgggag tactcgtgcc acatgtgggc    600
gaaaccccaa ttgcataccg caatgttctt cttcgtaaga acggtaataa gggagccggt    660
ggtcatagct atggcatcga tctaaagtct tatgacttag gtgacgagct tggcactgat    720
cccattgaag attatgaaca aaactggaac actaagcatg gcagtggtgc actccgtgaa    780
ctcactcgtg agctcaatgg aggtgcagtc actcgctatg tcgacaacaa tttctgtggc    840
ccagatgggt accctcttga ttgcatcaaa gatttctctcg cacgcgcggg caagtcaatg    900
tgcactcttt ccgaacaact tgattacatc gagtcgaaga gaggtgtcta ctgctgccgt    960
gaccatgagc atgaaattgc ctggttcact gagcgctctg ataagagcta cgagcaccag   1020
acacccttcg aaattaagag tgccaagaaa tttgacactt tcaaagggga atgcccaaag   1080
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt tcatggcag    1260 acgtgcgact ttctgaaagc cacttgtgaa cattgtggca ctgaaaattt agttattgaa    1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct gaatgagga tctccttgag   1620 atactgagtc gtgaacgtgt taacattaac attgttggcg attttcattt gaatgaagag    1680
gttgccatca ttttggcatc tttctctgct tctacaagtg cctttattga cactataaag    1740
agtcttgatt acaagtcttt caaaaccatt gttgagtcct gcggtaacta taagttacc    1800
```

```
aagggaaagc ccgtaaaagg tgcttggaac attggacaac agagatcagt tttaacacca    1860
ctgtgtggtt ttccctcaca ggctgctggt gttatcagat caattttttgc gcgcacactt   1920 gatgcagcaa accactcaat tcctgatttg caaagagcag ctgtcaccat acttgatggt    1980
atttctgaac agtcattacg tcttgtcgac gccatggttt atacttcaga cctgctcacc    2040
aacagtgtca ttattatggc atatgtaact ggtggtcttg tacaacagac ttctcagtgg    2100
ttgtctaatc ttttgggcac tactgttgaa aaactcaggc ctatctttga atggattgag    2160
gcgaaactta gtgcaggagt tgaatttctc aaggatgctt gggagattct caaatttctc    2220
attacaggtg tttttgacat cgtcaagggt caaatacagg ttgcttcaga taacatcaag    2280
gattgtgtaa aatgcttcat tgatgttgtt aacaaggcac tcgaaatgtg cattgatcaa    2340
gtcactatcg ctggcgcaaa gttgcgatca ctcaacttag gtgaagtctt catcgctcaa    2400
agcaagggac tttaccgtca gtgtatacgt ggcaaggagc agctgcaact actcatgcct    2460
cttaaggcac caaaagaagt aacctttctt gaaggtgatt cacatgacac agtacttacc    2520
tctgaggagg ttgttctcaa gaacggtgaa ctcgaagcac tcgagacgcc cgttgatagc    2580
ttcacaaatg gagctatcgt tggcacacca gtctgtgtaa atggcctcat gctcttagag    2640
attaaggaca agaacaata ctgcgcattg tctcctggtt tactggctac aaacaatgtc    2700
tttcgcttaa aggggggtgc accaattaaa ggtgtaacct ttggagaaga tactgtttgg    2760
gaagttcaag gttacaagaa tgtgagaatc acatttgagc ttgatgaacg tgttgacaaa    2820
gtgcttaatg aaaagtgctc tgtctacact gttgaatccg gtaccgaagt tactgagttt    2880
gcatgtgttg tagcagaggc tgttgtgaag actttacaac cagtttctga tctccttacc    2940
aacatgggta ttgatcttga tgagtggagt gtagctacat tctacttatt tgatgatgct    3000
ggtgaagaaa acttttcatc acgtatgtat tgttcctttt accctccaga tgaggaagaa    3060
gaggacgatg cagagtgtga ggaagaagaa attgatgaaa cctgtgaaca tgagtacggt    3120
acagaggatg attatcaagg tctccctctg gaatttggtg cctcagctga aacagttcga    3180
gttgaggaag aagaagagga agactggctg atgatactg ctgagcaatc agagattgag    3240
ccagaaccag aacctacacc tgaagaacca gttaatcagt ttactggtta tttaaaactt    3300
actgacaatg ttgccattaa atgtgttgac atcgttaagg aggcacaaag tgctaatcct    3360
atggtgattg taaatgctgc taacatacac ctgaaacatg gtggtggtgt agcaggtgca    3420
ctcaacaagg caaccaatgg tgccatgcaa aaggagagtg atgattacat taagctaaat    3480
ggccctctta cagtaggagg gtcttgtttg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag agccaccaa acacagaaga ttccaaaact    3840
gaggagaaat ctgtcgtaca aagcctgtc gatgtgaagc caaaaattaa ggcctgcatt    3900
gatgaggtta ccacaacact ggaagaaact aagtttctta ccaataagtt actcttgttt    3960
gctgatatca atggtaagct ttaccatgat tctcagaaca tgcttagagg tgaagatatg    4020
tctttccttg agaaggatgc accttacatg gtaggtgatg ttatcactag tggtgatatc    4080
acttgtgttg taatacccctc caaaaaggct ggtggcacta ctgagatgct ctcaagagct    4140
```

```
ttgaagaaag tgccagttga tgagtatata accacgtacc ctggacaagg atgtgctggt    4200
tatacacttg aggaagctaa gactgctctt aagaaatgca atctgcatt ttatgtacta    4260 ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca    4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagcccgt cgagtttcat cttgacggtg aggttctttc acttgacaaa    4860
ctaaagagtc tcttatccct gcgggaggtt aagactataa aagtgttcac aactgtggac    4920
aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg cttttaaacca cacaaagaaa    5160 tggaaatttc ctcaagttgg tggtttaact tcaattaaat gggctgataa caattgttat    5220
ttgtctagtg ttttattagc acttcaacag cttgaagtca aattcaatgc accagcactt    5280
caagaggctt attatagagc ccgtgctggt gatgctgcta acttttgtgc actcatactc    5340
gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagaccctc tatcgtattg acggagctca ccttacaaag    5760
atgtcagagt acaaaggacc agtgactgat gtttttctaca aggaaacatc ttacactaca    5820
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca aacacttggt gtttacgttg tctttggagt    6240
acaaagccag tagatacttc aaattcattt gaagttctgg cagtagaaga cacacaagga    6300
atggacaatc ttgcttgtga aagtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacaaag agttaggtca tgaggatctt    6480
atggctgctt atgtggaaaa cacaagcatt accattaaga aacctaatga gctttcacta    6540
```

-continued

```
gccttaggtt taaaaacaat tgccactcat ggtattgctg caattaatag tgttccttgg   6600
agtaaaattt tggcttatgt caaaccattc ttaggacaag cagcaattac aacatcaaat   6660
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740

catccgctct cccattttgt caatttagac aatttgagag ctaacaacac taaaggttca   7800
ctgcctatta atgtcatagt ttttgatggc aagtccaaat gcgacgagtc tgcttctaag   7860
tctgcttctg tgtactacag tcagctgatg tgccaaccta ttctgttgct tgaccaagct   7920
cttgtatcag acgttggaga tagtactgaa gtttccgtta agatgtttga tgcttatgtc   7980
gacacctttt cagcaacttt tagtgttcct atggaaaaac ttaaggcact tgttgctaca   8040
gctcacagcg agttagcaaa gggtgtagct ttagatggtg tcctttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
gcatggttta gccagcgtgg tggttcatac aaaaatgaca aaagctgccc tgtagtagct   8760
gctatcatta caagagagat tggtttcata gtgcctggct taccgggtac tgtgctgaga   8820
gcaatcaatg gtgacttctt gcattttcta cctcgtgttt ttagtgctgt tggcaacatt   8880
```

```
tgctacacac cttccaaact cattgagtat agtgattttg ctacctctgc ttgcgttctt    8940
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt ttgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgttttggg tgagtacaac    9420
catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt tgccatgtt ttctcctatt     9600
gtgcctttt ggataacagc aatctatgta ttctgtattt ctctgaagca ctgccattgg     9660
ttcttttaaca actatcttag gaaaagagtc atgtttaatg gagttacatt tagtaccttc    9720
gaggaggctg ctttgtgtac cttttgctc aacaaggaaa tgtacctaaa attgcgtagc     9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa   10020
gttgaagggt gcatggtaca agtaacctgt ggaactacaa ctcttaatgg attgtggttg   10080
gatgacacag tatactgtcc aagacatgtc atttgcacag cagaagacat gcttaatcct   10140
aactatgaag atctgctcat tcgcaaatcc aaccatagct ttcttgttca ggctggcaat   10200
gttcaacttc gtgttattgg ccattctatg caaaattgtc tgcttaggct taaagttgat   10260
acttctaacc ctaagacacc caagtataaa tttgtccgta tccaacctgg tcaaacattt   10320
tcagttctag catgctacaa tggttcacca tctggtgttt atcagtgtgc catgagacct   10380
aatcatacca ttaaaggttc tttccttaat ggatcatgtg gtagtgttgg ttttaacatt   10440
gattatgatt gcgtgtcttt ctgctatatg catcatatgg agcttccaac aggagtacac   10500
gctggtactg acttagaagg taaattctat ggtccatttg ttgacagaca aactgcacag   10560
gctgcaggta cagacacaac cataacatta atgttttggg catggctgta tgctgctgtt   10620
atcaatggtg ataggtggtt tcttaataga ttcaccacta cttttgaatga ctttaacctt   10680
gtggcaatga agtacaacta tgaaccttg acacaagatc atgttgacat attgggacct   10740
ctttctgctc aaacaggaat tgccgtctta gatatgtgtg ctgctttgaa agagctgctg   10800
cagaatggta tgaatggtcg tactatcctt ggtagcacta ttttagaaga tgagtttaca   10860
ccatttgatg ttgttagaca atgctctggt gttaccttcc aaggtaagtt caagaaaatt   10920
gttaagggca ctcatcattg gatgctttta actttcttga catcactatt gattcttgtt   10980
caaagtacac agtggtcact gttttttctt gtttacgaga atgctttctt gccatttact   11040
cttggtatta tggcaattgc tgcatgtgct atgctgcttg ttaagcataa gcacgcattc   11100
ttgtgcttgt ttctgttacc ttctcttgca acagttgctt actttaatat ggtctacatg   11160
cctgctagct gggtgatgcg tatcatgaca tggcttgaat tggctgacac tagcttgtct   11220
ggttataggc ttaaggattg tgttatgtat gcttcagctt tagttttgct tattctcatg   11280
```

```
acagctcgca ctgtttatga tgatgctgct agacgtgttt ggacactgat gaatgtcatt      11340
acacttgttt acaaagtcta ctatggtaat gctttagatc aagctatttc catgtgggcc      11400
ttagttattt ctgtaacctc taactattct ggtgtcgtta cgactatcat gttttttagct     11460 agagctatag tgtttgtgtg tgttgagtat tacccattgt tatttattac tggcaacacc      11520
ttacagtgta tcatgcttgt ttattgtttc ttaggctatt gttgctgctg ctactttggc      11580
cttttctgtt tactcaaccg ttacttcagg cttactcttg gtgtttatga ctacttggtc      11640
tctacacaag aatttaggta tatgaactcc caggggcttt tgcctcctaa gagtagtatt      11700
gatgctttca agcttaacat taagttgttg ggtattggag gtaaaccatg tatcaaggtt      11760
gctactgtac agtctaaaat gtctgacgta aagtgcacat ctgtggtact gctctcggtt      11820
cttcaacaac ttagagtaga gtcatcttct aaattgtggg cacaatgtgt acaactccac      11880
aatgatattc ttcttgcaaa agacacaact gaagctttcg agaagatggt ttctcttttg      11940
tctgttttgc tatccatgca gggtgctgta gacattaata ggttgtgcga ggaaatgctc      12000
gataaccgtg ctactcttca ggctattgct tcagaattta gttctttacc atcatatgcc      12060
gcttatgcca ctgcccagga ggcctatgag caggctgtag ctaatggtga ttctgaagtc      12120
gttctcaaaa agtaaagaa atctttgaat gtggctaaat ctgagtttga ccgtgatgct      12180
gccatgcaac gcaagttgga aaagatggca gatcaggcta tgacccaaat gtacaaacag      12240
gcaagatctg aggacaagag ggcaaaagta actagtgcta tgcaaacaat gctcttcact      12300
atgcttagga agcttgataa tgatgcactt aacaacatta tcaacaatgc gcgtgatggt      12360
tgtgttccac tcaacatcat accattgact acagcagcca aactcatggt tgttgtccct      12420
gattatggta cctacaagaa cacttgtgat ggtaacacct ttacatatgc atctgcactc      12480
tgggaaatcc agcaagttgt tgatgcggat agcaagattg ttcaacttag tgaaattaac      12540
atggacaatt caccaaattt ggcttggcct cttattgtta cagctctaag agccaactca      12600
gctgttaaac tacagaataa tgaactgagt ccagtagcac tacgacagat gtcctgtgcg      12660
gctggtacca cacaaacagc ttgtactgat gacaatgcac ttgcctacta taacaattcg      12720
aagggaggta ggtttgtgct ggcattacta tcagaccacc aagatctcaa atgggctaga      12780
ttccctaaga gtgatggtac aggtacaatt tacacagaac tggaaccacc ttgtaggttt      12840
gttacagaca caccaaaagg gcctaaagtg aaatacttgt acttcatcaa aggcttaaac      12900
aacctaaata gaggtatggt gctgggcagt ttagctgcta cagtacgtct tcaggctgga      12960
aatgctacag aagtacctgc caattcaact gtgctttcct tctgtgcttt tgcagtagac      13020
cctgctaaag catataagga ttacctagca agtggaggac aaccaatcac caactgtgtg      13080
aagatgttgt gtacacacac tggtacagga caggcaatta ctgtaacacc agaagctaac      13140
atggaccaag agtcctttgg tggtgcttca tgttgtctgt attgtagatg ccacattgac      13200
catccaaatc ctaaaggatt ctgtgacttg aaaggtaagt acgtccaaat acctaccact      13260
tgtgctaatg acccagtggg tttttacactt agaaacacag tctgtaccgt ctgcggaatg      13320
tggaaaggtt atggctgtag ttgtgaccaa ctccgcgaac ccttgatgca gtctgcggat      13380
gcatcaacgt ttttaaacgg gtttgcggtg taagtgcagc ccgtcttaca ccgtgcggca      13440
caggcactag tactgatgtc gtctacaggg cttttgatat ttacaacgaa aaagttgctg      13500
gttttgcaaa gttcctaaaa actaattgct gtcgcttcca ggagaaggat gaggaaggca      13560
atttattaga ctcttacttt gtagttaaga ggcatactat gtctaactac caacatgaag      13620
```

```
agactattta taacttggtt aaagattgtc cagcggttgc tgtccatgac ttttcaagt    13680
ttagagtaga tggtgacatg gtaccacata tatcacgtca gcgtctaact aaatacacaa    13740
tggctgattt agtctatgct ctacgtcatt ttgatgaggg taattgtgat acattaaaag    13800
aaatactcgt cacatacaat tgctgtgatg atgattattt caataagaag gattggtatg    13860
acttcgtaga gaatcctgac atcttacgcg tatatgctaa cttaggtgag cgtgtacgcc    13920
aatcattatt aaagactgta caattctgcg atgctatgcg tgatgcaggc attgtaggcg    13980
tactgacatt agataatcag gatcttaatg ggaactggta cgatttcggt gatttcgtac    14040
aagtagcacc aggctgcgga gttcctattg tggattcata ttactcattg ctgatgccca    14100
tcctcacttt gactagggca ttggctgctg agtcccatat ggatgctgat ctcgcaaaac    14160
cacttattaa gtgggatttg ctgaaatatg attttacgga agagagactt tgtctcttcg    14220
accgttattt taaatattgg gaccagacat accatcccaa ttgtattaac tgtttggatg    14280
ataggtgtat ccttcattgt gcaaacttta atgtgttatt ttctactgtg tttccaccta    14340
caagttttgg accactagta agaaaaatat tgtagatgg tgttcctttt gttgtttcaa    14400
ctggatacca ttttcgtgag ttaggagtcg tacataatca ggatgtaaac ttacatagct    14460
cgcgtctcag tttcaaggaa cttttagtgt atgctgctga tccagctatg catgcagctt    14520
ctggcaattt attgctagat aaacgcacta catgctttc agtagctgca ctaacaaaca    14580
atgttgcttt tcaaactgtc aaacccggta attttaataa agacttttat gactttgctg    14640
tgtctaaagg tttcttttaag gaaggaagtt ctgttgaact aaaacacttc ttctttgctc    14700
aggatggcaa cgctgctatc agtgattatg actattatcg ttataatctg ccaacaatgt    14760
gtgatatcag acaactccta ttcgtagttg aagttgttga taaatacttt gattgttacg    14820
atggtggctg tattaatgcc aaccaagtaa tcgttaacaa tctggataaa tcagctggtt    14880
tcccattaa taaatggggt aaggctagac tttattatga ctcaatgagt tatgaggatc    14940
aagatgcact tttcgcgtat actaagcgta atgtcatccc tactataact caaatgaatc    15000
ttaagtatgc cattagtgca aagaatagag ctcgcaccgt agctggtgtc tctatctgta    15060
gtactatgac aaatagacag tttcatcaga aattattgaa gtcaatagcc gccactagag    15120
gagctactgt ggtaattgga acaagcaagt tttacggtgg ctggcataat atgttaaaaa    15180
ctgtttacag tgatgtagaa actccacacc ttatgggttg ggattatcca aaatgtgaca    15240
gagccatgcc taacatgctt aggataatgg cctctcttgt tcttgctcgc aaacataaca    15300
cttgctgtaa cttatcacac cgtttctaca ggttagctaa cgagtgtgcg caagtattaa    15360
gtgagatggt catgtgtggc ggctcactat atgttaaacc aggtggaaca tcatccggtg    15420
atgctacaac tgcttatgct aatagtgtct ttaacatttg tcaagctgtt acagccatg    15480
taaatgcact tctttcaact gatggtaata agatagctga caagtatgtc cgcaatctac    15540
aacacaggct ctatgagtgt ctctatagaa atagggatgt tgatcatgaa ttcgtggatg    15600
agttttacgc ttacctgcgt aaacatttct ccatgatgat tctttctgat gatgccgttg    15660
tgtgctataa cagtaactat gcggctcaag gtttagtagc tagcattaag aactttaagg    15720
cagttcttta ttatcaaaat aatgtgttca tgtctgaggc aaaatgttgg actgagactg    15780
accttactaa aggacctcac gaattttgct cacagcatac aatgctagtt aaacaaggag    15840
atgattacgt gtacctgcct tacccagatc catcaagaat attaggcgca ggctgttttg    15900
tcgatgatat tgtcaaaaca gatggtacac ttatgattga aaggttcgtg tcactggcta    15960
ttgatgctta cccacttaca aaacatccta atcaggagta tgctgatgtc tttcacttgt    16020
```

```
atttacaata cattagaaag ttacatgatg agcttactgg ccacatgttg gacatgtatt    16080
ccgtaatgct aactaatgat aacacctcac ggtactggga acctgagttt tatgaggcta    16140
tgtacacacc acatacagtc ttgcaggctg taggtgcttg tgtattgtgc aattcacaga    16200
cttcacttcg ttgcggtgcc tgtattagga gaccattcct atgttgcaag tgctgctatg    16260
accatgtcat ttcaacatca cacaaattag tgttgtctgt taatccctat gtttgcaatg    16320
ccccaggttg tgatgtcact gatgtgacac aactgtatct aggaggtatg agctattatt    16380
gcaagtcaca taagcctccc attagttttc cattatgtgc taatggtcag gtttttggtt    16440
tatacaaaaa cacatgtgta ggcagtgaca atgtcactga cttcaatgcg atagcaacat    16500
gtgattggac taatgctggc gattacatac ttgccaacac ttgtactgag agactcaagc    16560
ttttcgcagc agaaacgctc aaagccactg aggaaacatt taagctgtca tatggtattg    16620
ccactgtacg cgaagtactc tctgacagag aattgcatct ttcatgggag gttggaaaac    16680
ctagaccacc attgaacaga aactatgtct ttactggtta ccgtgtaact aaaaatagta    16740
aagtacagat tggagagtac acctttgaaa aaggtgacta tggtgatgct gttgtgtaca    16800
gaggtactac gacatacaag ttgaatgttg gtgattactt tgtgttgaca tctcacactg    16860
taatgccact tagtgcacct actctagtgc cacaagagca ctatgtgaga attactggct    16920
tgtacccaac actcaacatc tcagatgagt tttctagcaa tgttgcaaat tatcaaaagg    16980
tcggcatgca aaagtactct acactccaag gaccacctgg tactggtaag agtcatttg    17040 ccatcggact tgctctctat tacccatctg ctcgcatagt gtatacggca tgctctcatg    17100
cagctgttga tgccctatgt gaaaaggcat taaaatattt gcccatagat aaatgtagta    17160
gaatcatacc tgcgcgtgcg cgcgtagagt gttttgataa attcaaagtg aattcaacac    17220
tagaacagta tgttttctgc actgtaaatg cattgccaga acaactgctg acattgtag    17280 tctttgatga aatctctatg gctactaatt atgacttgag tgttgtcaat gctagacttc    17340
gtgcaaaaca ctacgtctat attggcgatc ctgctcaatt accagccccc cgcacattgc    17400
tgactaaagg cacactagaa ccagaatatt ttaattcagt gtgcagactt atgaaaacaa    17460
taggtccaga catgttcctt ggaacttgtc gccgttgtcc tgctgaaatt gttgacactg    17520
tgagtgcttt agtttatgac aataagctaa aagcacacaa ggataagtca gctcaatgct    17580
tcaaaatgtt ctacaaaggt gttattacac atgatgtttc atctgcaatc aacagacctc    17640
aaataggcgt tgtaagagaa tttcttacac gcaatcctgc ttggagaaaa gctgttttta    17700 tctcaccta taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaatgt aactggactt tttaaggact    18000
gtagtaagat cattactggt cttcatccta cacaggcacc tacacacctc agcgttgata    18060
taaagttcaa gactgaagga ttatgtgttg acataccagg cataccaaag gacatgacct    18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
```

```
cagaattcac cagagttaat gcaaaacctc caccaggtga ccagtttaaa catcttatac  18420
cactcatgta taaaggcttg ccctggaatg tagtgcgtat taagatagta caaatgctca  18480
gtgatacact gaaaggattg tcagacagag tcgtgttcgt cctttgggcg catggctttg  18540
agcttacatc aatgaagtac tttgtcaaga ttggacctga aagaacgtgt tgtctgtgtg  18600
acaaacgtgc aacttgcttt tctacttcat cagatactta tgcctgctgg aatcattctg  18660
tgggttttga ctatgtctat aacccattta tgattgatgt tcagcagtgg ggctttacgg  18720
gtaaccttca gagtaaccat gaccaacatt gccaggtaca tggaaatgca catgtggcta  18780
gttgtgatgc tatcatgact agatgtttag cagtccatga gtgctttgtt aagcgcgttg  18840
attggtctgt tgaataccct attataggag atgaactgag ggttaattct gcttgcagaa  18900
aagtacaaca catggttgtg aagtctgcat tgcttgctga taagtttcca gttcttcatg  18960
acattggaaa tccaaaggct atcaagtgtg tgcctcaggc tgaagtagaa tggaagttct  19020
acgatgctca gccatgtagt gacaaagctt acaaaataga ggaactcttc tattcttatg  19080
ctacacatca cgataaattc actgatggtg tttgtttgtt ttggaattgt aacgttgatc  19140
gttacccagc caatgcaatt gtgtgtaggt ttgacacaag agtcttgtca aacttgaact  19200
taccaggctg tgatggtggt agtttgtatg tgaataagca tgcattccac actccagctt  19260
tcgataaaag tgcatttact aatttaaagc aattgccttt cttttactat tctgatagtc  19320
cttgtgagtc tcatggcaaa caagtagtgt cggatattga ttatgttcca ctcaaatctg  19380
ctacgtgtat tacacgatgc aatttaggtg gtgctgtttg cagacaccat gcaaatgagt  19440
accgacagta cttggatgca tataatatga tgatttctgc tggatttagc ctatggattt  19500
acaaacaatt tgatacttat aacctgtgga atacatttac caggttacag agtttagaaa  19560
atgtggctta taatgttgtt aataaaggac actttgatgg acacgccggc gaagcacctg  19620
tttccatcat taataatgct gtttacacaa aggtagatgg tattgatgtg agatctttg   19680 aaaataagac aacacttcct gttaatgttg catttgagct ttgggctaag cgtaacatta  19740
aaccagtgcc agagattaag atactcaata atttgggtgt tgatatcgct gctaatactg  19800
taatctggga ctacaaaaga gaagccccag cacatgtatc tacaataggt gtctgcacaa  19860
tgactgacat tgccaagaaa cctactgaga gtgcttgttc ttcacttact gtcttgtttg  19920
atggtagagt ggaaggacag gtagaccttt ttagaaacgc ccgtaatggt gttttaataa  19980
cagaaggttc agtcaaaggt ctaacacctt caaagggacc agcacaagct agcgtcaatg  20040
gagtcacatt aattggagaa tcagtaaaaa cacagtttaa ctactttaag aaagtagacg  20100
gcattattca acagttgcct gaaacctact ttactcagag cagagactta gaggatttta  20160
agcccagatc acaaatggaa actgactttc tcgagctcgc tatggatgaa ttcatacagc  20220
gatataagct cgagggctat gccttcgaac acatcgttta tggagatttc agtcatggac  20280
aacttggcgg tcttcattta atgataggct tagccaagcg ctcacaagat tcaccactta  20340
aattagagga ttttatccct atggacagca cagtgaaaaa ttacttcata acagatgcgc  20400
aaacaggttc atcaaaatgt gtgtgttctg tgattgatct tttacttgat gactttgtcg  20460
agataataaa gtcacaagat tgtcagtgat ttcaaaagt ggtcaaggtt acaattgact  20520
atgctgaaat tcattcatg ctttggtgta aggatggaca tgttgaaacc ttctacccaa  20580
aactacaagc aagtcaagcg tggcaaccag gtgttgcgat gcctaacttg tacaagatgc  20640
aaagaatgct tcttgaaaag tgtgaccttc agaattatgg tgaaaatgct gttataccaa  20700
aaggaataat gatgaatgtc gcaaagtata ctcaactgtg tcaatactta aatacactta  20760
```

```
ctttagctgt accctacaac atgagagtta ttcactttgg tgctggctct gataaaggag    20820
ttgcaccagg tacagctgtg ctcagacaat ggttgccaac tggcacacta cttgtcgatt    20880
cagatcttaa tgacttcgtc tccgacgcag attctacttt aattggagac tgtgcaacag    20940
tacatacggc taataaatgg gaccttatta ttagcgatat gtatgaccct aggaccaaac    21000
atgtgacaaa agagaatgac tctaaagaag gttttttcac ttatctgtgt ggatttataa    21060
agcaaaaact agccctgggt ggttctatag ctgtaaagat aacagagcat tcttggaatg    21120
ctgaccttta caagcttatg gccatttcct catggtggac agcttttgtt acaaatgtaa    21180
atgcatcatc atcggaagca tttttaattg gggctaacta tcttggcaag ccgaaggaac    21240
aaattgatgg ctataccatg catgctaact acatttctg gaggaacaca aatcctatcc     21300
agttgtcttc ctattcactc tttgacatga gcaaatttcc tcttaaatta gaggaactg     21360
ctgtaatgtc tcttaaggag aatcaaatca atgatatgat ttattctctt ctggaaaaag    21420
gtaggcttat cattagagaa acaacagag ttgtggtttc aagtgatatt cttgttaaca     21480
actaaacgaa catgtttatt ttcttattat ttcttactct cactagtggt agtgaccttg    21540
accggtgcac cacttttgat gatgttcaag ctcctaatta cactcaacat acttcatcta    21600
tgagggggt ttactatcct gatgaaattt ttagatcaga cactctttat ttaactcagg     21660
atttatttct tccatttat tctaatgtta cagggtttca tactattaat catacgtttg     21720
gcaaccctgt cataccttt aaggatggta tttatttgc tgccacagag aaatcaaatg      21780
ttgtccgtgg ttgggttttt ggttctacca tgaacaacaa gtcacagtcg gtgattatta   21840
ttaacaattc tactaatgtt gttatacgag catgtaactt tgaattgtgt gacaacccttt  21900
tctttgctgt ttctaaaccc atgggtacac agacacatac tatgatattc gataatgcat   21960
ttaattgcac tttcgagtac atatctgatg ccttttcgct tgatgtttca gaaaagtcag   22020
gtaattttaa acacttacga gagttttgtgt ttaaaaataa agatgggttt ctctatgttt  22080
ataagggcta tcaacctata gatgtagttc gtgatctacc ttctggtttt aacactttga   22140
aacctatttt taagttgcct cttggtatta acattacaaa ttttagagcc attcttacag   22200
cctttttcacc tgctcaagac atttggggca cgtcagctgc agcctatttt gttggctatt  22260
taaagccaac tacattatg ctcaagtatg atgaaaatgg tacaatcaca gatgctgttg    22320
attgttctca aaatccactt gctgaactca aatgctctgt taagagcttt gagattgaca   22380
aaggaattta ccagacctct aatttcaggg ttgttccctc aggagatgtt gtgagattcc   22440
ctaatattac aaacttgtgt ccttttggag aggttttaa tgctactaaa ttcccttctg    22500
tctatgcatg ggagagaaaa aaaatttcta attgtgttgc tgattactct gtgctctaca   22560
actcaacatt ttttttcaacc tttaagtgct atggcgtttc tgccactaag ttgaatgatc   22620
tttgcttctc caatgtctat gcagattctt ttgtagtcaa gggagatgat gtaagacaaa   22680
tagcgccagg acaaactggt gttattgctg attataatta taaattgcca gatgatttca   22740
tgggttgtgt ccttgcttgg aatactagga acattgatgc tacttcaact ggtaattata   22800
attataaata taggtatctt agacatggca agcttaggcc ctttgagaga gacatatcta   22860
atgtgccttt ctcccctgat ggcaaacctt gcaccccacc tgctcttaat tgttattggc   22920
cattaaatga ttatggtttt tacaccacta ctggcattgg ctaccaacct tacagagttg   22980
tagtactttc ttttgaactt ttaaatgcac cggccacggt ttgtggacca aaattatcca   23040
ctgaccttat taagaaccag tgtgtcaatt ttaattttaa tggactcact ggtactggtg   23100
```

```
tgttaactcc ttcttcaaag agatttcaac catttcaaca atttggccgt gatgtttctg  23160
atttcactga ttccgttcga gatcctaaaa catctgaaat attagacatt tcaccttgcg  23220
cttttggggg tgtaagtgta attacacctg aacaaatgc ttcatctgaa gttgctgttc  23280
tatatcaaga tgttaactgc actgatgttt ctacagcaat tcatgcagat caactcacac  23340
cagcttggcg catatattct actggaaaca atgtattcca gactcaagca ggctgtctta  23400
taggagctga gcatgtcgac acttcttatg agtgcgacat tcctattgga gctggcattt  23460
gtgctagtta ccatacagtt tctttattac gtagtactag ccaaaaatct attgtggctt  23520
atactatgtc tttaggtgct gatagttcaa ttgcttactc taataacacc attgctatac  23580
ctactaactt tcaattagc attactacag aagtaatgcc tgtttctatg ctaaaacct  23640 ccgtagattg taatatgtac atctgcggag attctactga atgtgctaat ttgcttctcc  23700
aatatggtag cttttgcaca caactaaatc gtgcactctc aggtattgct gctgaacagg  23760
atcgcaacac acgtgaagtg ttcgctcaag tcaaacaaat gtacaaaacc ccaacttga  23820 aatattttgg tggttttaat ttttcacaaa tattacctga ccctctaaag ccaactaaga  23880
ggtcttttat tgaggacttg ctctttaata aggtgacact cgctgatgct ggcttcatga  23940
agcaatatgg cgaatgccta ggtgatatta atgctagaga tctcatttgt gcgcagaagt  24000
tcaatggact tacagtgttg ccacctctgc tcactgatga tatgattgct gcctacactg  24060
ctgctctagt tagtggtact gccactgctg gatggacatt tggtgctggc gctgctcttc  24120
aaataccttt tgctatgcaa atggcatata ggttcaatgg cattggagtt acccaaaatg  24180
ttctctatga gaaccaaaaa caaatcgcca accaatttaa caaggcgatt agtcaaattc  24240
aagaatcact tacaacaaca tcaactgcat tgggcaagct gcaagacgtt gttaaccaga  24300
atgctcaagc attaaacaca cttgttaaac aacttagctc taatttggt gcaatttcaa  24360 gtgtgctaaa tgatatcctt tcgcgacttg ataaagtcga ggcggaggta caaattgaca  24420
ggttaattac aggcagactt caaagccttc aaacctatgt aacacaacaa ctaatcaggg  24480
ctgctgaaat cagggcttct gctaatcttg ctgctactaa aatgtctgag tgtgttcttg  24540
gacaatcaaa aagagttgac ttttgtggaa agggctacca ccttatgtcc ttcccacaag  24600
cagccccgca tggtgttgtc ttcctacatg tcacgtatgt gccatcccag gagaggaact  24660
tcaccacagc gccagcaatt tgtcatgaag gcaaagcata cttccctcgt gaaggtgttt  24720
ttgtgtttaa tggcacttct tggtttatta cacagaggaa cttctttct ccacaaataa  24780 ttactacaga caatacattt gtctcaggaa attgtgatgt cgttattggc atcattaaca  24840
acacagttta tgatcctctg caacctgagc ttgactcatt caaagaagag ctggacaagt  24900
acttcaaaaa tcatacatca ccagatgttg atcttggcga catttcaggc attaacgctt  24960
ctgtcgtcaa cattcaaaaa gaaattgacc gcctcaatga ggtcgctaaa aatttaaatg  25020
aatcactcat tgaccttcaa gaattgggaa atatgagca atatattaaa tggccttggt  25080
atgtttggct cggcttcatt gctggactaa ttgccatcgt catggttaca atcttgcttt  25140
gttgcatgac tagttgttgc agttgcctca agggtgcatg ctcttgtggt tcttgctgca  25200
agtttgatga ggatgactct gagccagttc tcaagggtgt caaattacat tacacataaa  25260
cgaacttatg gatttgttta tgagatttt tactcttaga tcaattactg cacagccagt  25320
aaaaattgac aatgcttctc ctgcaagtac tgttcatgct acagcaacga taccgctaca  25380
agcctcactc ccttcggat ggcttgttat tggcgttgca tttcttgctg tttttcagag  25440
cgctaccaaa ataattgcgc tcaataaaag atggcagcta gccctttata agggcttcca  25500
```

```
gttcatttgc aatttactgc tgctatttgt taccatctat tcacatcttt tgcttgtcgc    25560
tgcaggtatg gaggcgcaat ttttgtacct ctatgccttg atatattttc tacaatgcat    25620
caacgcatgt agaattatta tgagatgttg gctttgttgg aagtgcaaat ccaagaaccc    25680
attactttat gatgccaact actttgtttg ctggcacaca cataactatg actactgtat    25740
accatataac agtgtcacag atacaattgt cgttactgaa ggtgacggca tttcaacacc    25800
aaaactcaaa gaagactacc aaattggtgg ttattctgag gataggcact caggtgttaa    25860
agactatgtc gttgtacatg gctatttcac cgaagtttac taccagcttg agtctacaca    25920
aattactaca gacactggta ttgaaaatgc tacattcttc atctttaaca agcttgttaa    25980
agacccaccg aatgtgcaaa tacacacaat cgacggctct tcaggagttg ctaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt cttttttcttg ctttcgtggt attcttgcta gtcacactag ccatccttac    26220
tgcgcttcga ttgtgtgcgt actgctgcaa tattgttaac gtgagtttag taaaaccaac    26280
ggtttacgtc tactcgcgtg ttaaaaatct gaactcttct gaaggagttc ctgatcttct    26340
ggtctaaacg aactaactat tattattatt ctgtttggaa ctttaacatt gcttatcatg    26400
gcagacaacg gtactattac cgttgaggag cttaaacaac tcctggaaca atggaaccta    26460
gtaataggtt tcctattcct agcctggatt atgttactac aatttgccta ttctaatcgg    26520
aacaggtttt tgtacataat aaagcttgtt ttcctctggc tcttgtggcc agtaacactt    26580
gcttgttttg tgcttgctgc tgtctacaga attaattggg tgactggcgg gattgcgatt    26640
gcaatggctt gtattgtagg cttgatgtgg cttagctact tcgttgcttc cttcaggctg    26700
tttgctcgta cccgctcaat gtggtcattc aacccagaaa caaacattct tctcaatgtg    26760
cctctccggg ggacaattgt gaccagaccg ctcatggaaa gtgaacttgt cattggtgct    26820
gtgatcattc gtggtcactt gcgaatggcc ggacactccc tagggcgctg tgacattaag    26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
taagtgacaa cagatgtttc atcttgttga cttccaggtt acaatagcag agatattgat    27120
tatcattatg aggactttca ggattgctat ttggaatctt gacgttataa taagttcaat    27180
agtgagacaa ttatttaagc ctctaactaa gaagaattat tcggagttag atgatgaaga    27240
acctatggag ttagattatc cataaaacga acatgaaaat tattctcttc ctgacattga    27300
ttgtatttac atcttgcgag ctatatcact atcaggagtg tgttagaggt acgactgtac    27360
tactaaaaga accttgccca tcaggaacat acgagggcaa ttcaccattt caccctcttg    27420
ctgacaataa atttgcacta acttgcacta gcacacactt tgcttttgct tgtgctgacg    27480
gtactcgaca tacctatcag ctgcgtgcaa gatcagtttc accaaaactt ttcatcagac    27540
aagaggaggt tcaacaagag ctctactcgc cactttttct cattgttgct gctctagtat    27600
ttttaatact tgcttcacc attaagagaa agacagaatg aatgagctca ctttaattga    27660
cttctatttg tgcttttag cctttctgct attccttgtt ttaataatgc ttattatatt    27720
ttggttttca ctcgaaatcc aggatctaga agaaccttgt accaaagtct aaacgaacat    27780
gaaacttctc attgttttga cttgtatttc tctatgcagt tgcatatgca ctgtagtaca    27840
```

```
gcgctgtgca tctaataaac ctcatgtgct tgaagatcct tgtaaggtac aacactaggg   27900
gtaatactta tagcactgct tggctttgtg ctctaggaaa ggttttacct tttcatagat   27960
ggcacactat ggttcaaaca tgcacaccta atgttactat caactgtcaa gatccagctg   28020
gtggtgcgct tatagctagg tgttggtacc ttcatgaagg tcaccaaact gctgcattta   28080
gagacgtact tgttgtttta aataaacgaa caaattaaaa tgtctgataa tggaccccaa   28140
tcaaaccaac gtagtgcccc ccgcattaca tttggtggac ccacagattc aactgacaat   28200
aaccagaatg gaggacgcaa tggggcaagg ccaaaacagc gccgacccca aggtttaccc   28260
aataatactg cgtcttggtt cacagctctc actcagcatg gcaaggagga acttagattc   28320
cctcgaggcc agggcgttcc aatcaacacc aatagtggtc cagatgacca aattggctac   28380
taccgaagag ctacccgacg agttcgtggt ggtgacggca aaatgaaaga gctcagcccc   28440
agatggtact tctattacct aggaactggc ccagaagctt cacttcccta cggcgctaac   28500
aaagaaggca tcgtatgggt tgcaactgag ggagccttga atacacccaa agaccacatt   28560
ggcacccgca atcctaataa caatgctgcc accgtgctac aacttcctca aggaacaaca   28620
ttgccaaaag gcttctacgc agagggaagc agaggcggca gtcaagcctc ttctcgctcc   28680
tcatcacgta gtcgcggtaa ttcaagaaat tcaactcctg gcagcagtag gggaaattct   28740
cctgctcgaa tggctagcgg aggtggtgaa actgccctcg cgctattgct gctagacaga   28800
ttgaaccagc ttgagagcaa agtttctggt aaaggccaac aacaacaagg ccaaactgtc   28860
actaagaaat ctgctgctga ggcatctaaa aagcctcgcc aaaaacgtac tgccacaaaa   28920
cagtacaacg tcactcaagc atttgggaga cgtggtccag aacaaaccca aggaaatttc   28980
ggggaccaag acctaatcag acaaggaact gattacaaac attggccgca aattgcacaa   29040
tttgctccaa gtgcctctgc attctttgga atgtcacgca ttggcatgga agtcacacct   29100
tcggaacat ggctgactta tcatggagcc attaaattgg atgacaaaga tccacaattc   29160
aaagacaacg tcatactgct gaacaagcac attgacgcat acaaaacatt cccaccaaca   29220
gagcctaaaa aggacaaaaa gaaaaagact gatgaagctc agcctttgcc gcagagacaa   29280
aagaagcagc ccactgtgac tcttcttcct gcggctgaca tggatgattt ctccagacaa   29340
cttcaaaatt ccatgagtgg agcttctgct gattcaactc aggcataaac actcatgatg   29400
accacacaag gcagatgggc tatgtaaacg ttttcgcaat tccgtttacg atacatagtc   29460
tactcttgtg cagaatgaat tctcgtaact aaacagcaca agtaggttta gttaacttta   29520
atctcacata gcaatcttta atcaatgtgt aacattaggg aggacttgaa agagccacca   29580
cattttcatc gaggccacgc ggagtacgat cgagggtaca gtgaataatg ctagggagag   29640
ctgcctatat ggaagagccc taatgtgtaa aattaatttt agtagtgcta tccccatgtg   29700
attttaatag cttcttagga gaatgacaaa aaaaaaaaa aaaaaaaaaa a           29751
```

<210> SEQ ID NO 5
<211> LENGTH: 548
<212> TYPE: PRT
<213> ORGANISM: Caenorhabditis sp.

<400> SEQUENCE: 5

```
Met Glu Glu Glu Glu Trp Arg Arg Arg Leu Ser Ala Ala Ile Arg Arg
1               5                   10                  15

Glu Asp Glu Gly Ser Leu Glu Glu Asp Glu Glu Asp Glu Gly Phe Ile
            20                  25                  30

Leu His Pro Leu Cys Arg Thr Gly Pro Leu Gln Met Thr Val Lys Ala
```

-continued

```
                35                  40                  45
Ser Asn Ser Thr Thr Thr Leu Thr Pro Ser Ser Thr Thr Thr Ser
        50                  55                  60

Pro Ser Met Pro Ser Ser Pro Ser Asp Ser Pro Ser Asp Asp Phe Ser
 65                  70                  75                  80

Asp Asp Thr Asn Thr Ser Gly Val Phe Pro Leu Thr Thr Ala Leu Ser
                    85                  90                  95

Phe Pro Val Ala Pro Leu Ser Pro Arg Asn Thr Thr Ser Ser Ile Thr
                100                 105                 110

Thr Gly Leu Val Lys Lys Arg Arg Ser Ser Ser Pro Glu Asp Ile
            115                 120                 125

Cys Arg Glu Lys Ile Pro His Ile Leu Leu Lys Thr Ser Ser Gly Val
        130                 135                 140

Val Val Pro Leu Ala Ser Arg Gly Gln Arg Ala Pro Ala Ile Thr Leu
145                 150                 155                 160

Gln Asn Pro Pro Pro Ser Ala Ala Ile Arg Thr Val Pro Pro Ser
                    165                 170                 175

Phe Ser Thr Phe Ser Val Arg Ser Leu Pro Phe Lys Thr Pro Asn Cys
                180                 185                 190

Gly Ser Lys Asp Asp Thr Asp Ala Glu Asn Met Glu Gly Leu Asp Asp
            195                 200                 205

Asp Tyr Leu Arg Gln Pro Thr Thr Ser Thr Ser Ala Pro Val Ser Pro
        210                 215                 220

Ile Asp His Arg Gln Val Arg Arg Gly Gly Arg Gly Val Val Val Glu
225                 230                 235                 240

Ser Gln Val Pro Asn Phe Thr Ala Glu Ile Phe Trp Leu Lys Thr Gln
                    245                 250                 255

Leu Ser Asp His Trp Ser Met Lys Trp Leu Phe Gln Asn Thr Ala Cys
                260                 265                 270

Leu Asp Asp Phe Asp Arg Ile Lys Thr Leu Gly Thr Gly Ser Phe Gly
            275                 280                 285

Arg Val Met Leu Val Lys His Lys Gln Ser Gly Asn Tyr Tyr Ala Met
        290                 295                 300

Lys Ile Leu Asp Lys Gln Lys Val Val Lys Leu Lys Gln Val Glu His
305                 310                 315                 320

Thr Leu Asn Glu Lys Arg Ile Leu Gln Ala Ile Asp Phe Pro Phe Leu
                    325                 330                 335

Val Asn Met Thr Phe Ser Phe Lys Asp Asn Ser Asn Leu Tyr Met Val
                340                 345                 350

Leu Glu Phe Ile Ser Gly Gly Glu Met Phe Ser His Leu Arg Arg Ile
            355                 360                 365

Gly Arg Phe Ser Glu Pro His Ser Arg Phe Tyr Ala Ala Gln Ile Val
        370                 375                 380

Leu Ala Phe Glu Tyr Leu His Ser Leu Asp Leu Ile Tyr Arg Asp Leu
385                 390                 395                 400

Lys Pro Glu Asn Leu Leu Ile Asp Ser Thr Gly Tyr Leu Lys Ile Thr
                    405                 410                 415

Asp Phe Gly Phe Ala Lys Arg Val Lys Gly Arg Thr Trp Thr Leu Cys
                420                 425                 430

Gly Thr Pro Glu Tyr Leu Ala Pro Glu Ile Ile Leu Ser Lys Gly Tyr
            435                 440                 445

Asn Lys Ala Val Asp Trp Trp Ala Leu Gly Val Leu Ile Tyr Glu Met
450                 455                 460
```

```
Ala Ala Gly Tyr Pro Pro Phe Phe Ala Asp Gln Pro Ile Gln Ile Tyr
465                 470                 475                 480

Glu Lys Ile Val Ser Gly Lys Val Lys Phe Pro Ser His Phe Ser Asn
                485                 490                 495

Glu Leu Lys Asp Leu Leu Lys Asn Leu Leu Gln Val Asp Leu Thr Lys
                500                 505                 510

Arg Tyr Gly Asn Leu Lys Asn Gly Val Ala Asp Ile Lys Asn His Lys
                515                 520                 525

Trp Phe Gly Ser Thr Asp Trp Ile Ala Ile Tyr Gln Lys Lys Val Ser
            530                 535                 540

Ser Tyr Pro Ile
545

<210> SEQ ID NO 6
<211> LENGTH: 480
<212> TYPE: PRT
<213> ORGANISM: Aspergillus sp.

<400> SEQUENCE: 6

Met Pro Ser Leu Gly Gly Leu Leu Lys Lys Arg Arg Thr Lys Asp Ser
1               5                   10                  15

Gln Thr Leu Ser Lys Glu Leu Glu Ala Gly Ser Ala Gln Thr Gln Thr
                20                  25                  30

Ser Pro Asn Ala Ala Glu Asp His His Asn His Asn His His Gln His
            35                  40                  45

His His His Leu Phe His His His Gln Pro Gln Pro Ala Thr Asn
    50                  55                  60

Ser Gly Ser Ala Ala Asn Thr Pro Pro Gln Pro Gln Asp Ser Val Pro
65                  70                  75                  80

Gln Gln Ser Asn Arg Ser Ser Gly Ala Glu Lys Ser Ser Asp Gly Gln
                85                  90                  95

Val Ala Ser Met Gln Ser Ala Val Thr Gln Ala Ser Pro Ser Ala His
                100                 105                 110

His Thr Ser Gly Leu Pro Gln Pro Asn Ala Asn Ala Ser Ile Gln
            115                 120                 125

Asn Ile Ile Asn Pro Ser Gln Gln Gly Ala Met His Ser Ala Ser Ser
130                 135                 140

Gly His Thr Gln Ser His His Ala Gly Arg Ser Asp Ala Arg Thr Thr
145                 150                 155                 160

Lys Gly Lys Tyr Ser Leu Asp Asp Phe Ser Leu Gln Arg Thr Leu Gly
                165                 170                 175

Thr Gly Ser Phe Gly Arg Val His Leu Val Gln Ser Lys His Asn His
                180                 185                 190

Arg Phe Tyr Ala Val Lys Val Leu Lys Lys Ala Gln Val Val Lys Met
            195                 200                 205

Lys Gln Ile Glu His Thr Asn Asp Glu Arg Arg Met Leu Asn Arg Val
    210                 215                 220

Arg His Pro Phe Leu Ile Thr Leu Trp Gly Thr Trp Gln Asp Ser Arg
225                 230                 235                 240

Asn Leu Tyr Met Val Met Asp Phe Val Glu Gly Gly Glu Leu Phe Ser
                245                 250                 255

Leu Val Arg Lys Ser Gln Arg Phe Pro Asn Pro Val Ala Lys Phe Tyr
                260                 265                 270

Ala Ala Glu Val Thr Leu Ala Leu Glu Tyr Leu His Thr Gln Asn Ile
```

```
                275                 280                 285
Ile Tyr Arg Asp Leu Lys Pro Glu Asn Leu Leu Asp Arg His Gly
        290                 295                 300

His Leu Lys Ile Thr Asp Phe Gly Phe Ala Lys Glu Val Pro Asp Ile
305                 310                 315                 320

Thr Trp Thr Leu Cys Gly Thr Pro Asp Tyr Leu Ala Pro Glu Val Val
                325                 330                 335

Ser Ser Lys Gly Tyr Asn Lys Ser Val Asp Trp Trp Ser Leu Gly Ile
            340                 345                 350

Leu Ile Phe Glu Met Leu Cys Gly Phe Thr Pro Phe Trp Asp Ser Gly
        355                 360                 365

Ser Pro Val Lys Ile Tyr Glu Asn Ile Leu Arg Gly Arg Val Lys Tyr
    370                 375                 380

Pro Pro Tyr Leu His Pro Asp Ala Val Asp Leu Leu Ser Gln Leu Ile
385                 390                 395                 400

Thr Ala Asp Leu Thr Lys Arg Leu Gly Asn Leu His Gly Gly Ser Asp
                405                 410                 415

Asp Val Lys Asn His Pro Trp Phe Ala Glu Val Thr Trp Asp Arg Leu
            420                 425                 430

Ala Arg Lys Asp Ile Asp Ala Pro Tyr Val Pro Pro Ile Arg Gly Gly
        435                 440                 445

Gln Gly Asp Ala Ser Gln Tyr Asp Arg Tyr Pro Glu Glu Thr Glu Gln
    450                 455                 460

Tyr Gly Met Ala Gly Glu Asp Pro His Gly His Leu Phe Pro Asp Phe
465                 470                 475                 480

<210> SEQ ID NO 7
<211> LENGTH: 398
<212> TYPE: PRT
<213> ORGANISM: Saccharomyces sp.

<400> SEQUENCE: 7

Met Tyr Val Asp Pro Met Asn Asn Glu Ile Arg Lys Leu Ser Ile
1               5                   10                  15

Thr Ala Lys Thr Glu Thr Thr Pro Asp Asn Val Gly Gln Asp Ile Pro
                20                  25                  30

Val Asn Ala His Ser Val His Glu Cys Ser Ser Asn Thr Pro Val
            35                  40                  45

Glu Ile Asn Gly Arg Asn Ser Gly Lys Leu Lys Glu Ala Ser Ala
    50                  55                  60

Gly Ile Cys Leu Val Lys Lys Pro Met Leu Gln Tyr Arg Asp Thr Ser
65                  70                  75                  80

Gly Lys Tyr Ser Leu Ser Asp Phe Gln Ile Leu Arg Thr Leu Gly Thr
            85                  90                  95

Gly Ser Phe Gly Arg Val His Leu Ile Arg Ser Asn His Asn Gly Arg
                100                 105                 110

Phe Tyr Ala Leu Lys Thr Leu Lys Lys His Thr Ile Val Lys Leu Lys
            115                 120                 125

Gln Val Glu His Thr Asn Asp Glu Arg Arg Met Leu Ser Ile Val Ser
    130                 135                 140

His Pro Phe Ile Ile Arg Met Trp Gly Thr Phe Gln Asp Ser Gln Gln
145                 150                 155                 160

Val Phe Met Val Met Asp Tyr Ile Glu Gly Gly Glu Leu Phe Ser Leu
                165                 170                 175
```

```
Leu Arg Lys Ser Gln Arg Phe Pro Asn Pro Val Ala Lys Phe Tyr Ala
            180                 185                 190

Ala Glu Val Cys Leu Ala Leu Glu Tyr Leu His Ser Lys Asp Ile Ile
        195                 200                 205

Tyr Arg Asp Leu Lys Pro Glu Asn Ile Leu Leu Asp Lys Asn Gly His
    210                 215                 220

Ile Lys Ile Thr Asp Phe Gly Phe Ala Lys Tyr Val Pro Asp Val Thr
225                 230                 235                 240

Tyr Thr Leu Cys Gly Thr Pro Asp Tyr Ile Ala Pro Glu Val Val Ser
                245                 250                 255

Thr Lys Pro Tyr Asn Lys Ser Val Asp Trp Trp Ser Phe Gly Val Leu
            260                 265                 270

Ile Tyr Glu Met Leu Ala Gly Tyr Thr Pro Phe Tyr Asn Ser Asn Thr
        275                 280                 285

Met Lys Thr Tyr Glu Asn Ile Leu Asn Ala Glu Leu Lys Phe Pro Pro
    290                 295                 300

Phe Phe His Pro Asp Ala Gln Asp Leu Leu Lys Lys Leu Ile Thr Arg
305                 310                 315                 320

Asp Leu Ser Glu Arg Leu Gly Asn Leu Gln Asn Gly Ser Glu Asp Val
                325                 330                 335

Lys Asn His Pro Trp Phe Asn Glu Val Ile Trp Glu Lys Leu Leu Ala
            340                 345                 350

Arg Tyr Ile Glu Thr Pro Tyr Glu Pro Pro Ile Gln Gln Gly Gln Gly
        355                 360                 365

Asp Thr Ser Gln Phe Asp Arg Tyr Pro Glu Glu Phe Asn Tyr Gly
    370                 375                 380

Ile Gln Gly Glu Asp Pro Tyr Met Asp Leu Met Lys Glu Phe
385                 390                 395

<210> SEQ ID NO 8
<211> LENGTH: 515
<212> TYPE: PRT
<213> ORGANISM: Cryptococcus sp.

<400> SEQUENCE: 8

Met Phe Gln Lys Val Ser Asp Lys Phe His Arg Lys Gln Gln Ser Ser
1               5                   10                  15

Thr Ser Pro Gly Lys Thr Gln Gln Val Pro Asn Ser Pro Ser Ser Val
            20                  25                  30

Leu Ala Lys Ala Asn Ser Gln Ala Gln Gln Ala Tyr Ser Ser Gln Asp
        35                  40                  45

His Ser Pro Met Glu Gly Ile Gln Ser Asp Ser Thr His Ile Gln Gln
    50                  55                  60

Pro Met Ala Thr Gln Lys Ala Pro Ile Val Gly Pro Ser Thr Ser Thr
65                  70                  75                  80

Ser Leu Ser Thr Val Pro Val Gln Asp Gly Thr Leu Pro Leu Thr Pro
                85                  90                  95

Gly Ala Gln Gly Met Leu Ala Gly Thr Thr Asp Gly His Arg Gln Val
            100                 105                 110

Gln Ser Pro Val Ser Arg Ser Ser Ala Gly Glu Asp Lys Met Arg
        115                 120                 125

Glu Lys Ala Arg Asp Ala Gln Glu Gln Ala Gln Ala Gln Ala Asn
    130                 135                 140

Leu His Arg Val Thr Gln Gln Ala Arg Val Ala Ala Ile Asn Ala Ala
145                 150                 155                 160
```

```
Ala Thr Gln Ala Ala Leu Glu Thr Ala Thr Gln Leu Pro Ala Thr Ala
                165                 170                 175

Arg Val Pro Thr Ser Gly Thr Gly Ala Glu Pro Gly Gln Ala Arg Arg
            180                 185                 190

Lys Thr Ala Gly Arg Tyr Ala Leu Ser Asp Phe Leu Ile Glu Arg Thr
        195                 200                 205

Leu Gly Thr Gly Ser Phe Gly Arg Val His Leu Val Arg Ser Arg His
    210                 215                 220

Asn Gly Arg Phe Tyr Ala Val Lys Val Leu Asn Lys Glu Lys Val Ile
225                 230                 235                 240

Lys Met Lys Gln Val Glu His Thr Asn Ser Glu Arg Glu Met Leu Val
                245                 250                 255

Arg Val Arg His Pro Phe Leu Val Leu Trp Gly Thr Phe Gln Asp
            260                 265                 270

Val Asn Asn Leu Tyr Met Val Met Asp Phe Val Ala Gly Gly Glu Leu
        275                 280                 285

Phe Ser Leu Leu Arg Lys Ser Gln Arg Phe Pro Asn Ser Val Ala Lys
    290                 295                 300

Phe Tyr Ala Ala Glu Val Ala Leu Ala Leu Asp Tyr Leu His Ser Leu
305                 310                 315                 320

Asp Ile Ile Tyr Arg Asp Leu Lys Pro Glu Asn Leu Leu Leu Gly Ala
                325                 330                 335

Asp Gly His Val Lys Val Thr Asp Phe Gly Phe Ala Lys Tyr Val Pro
            340                 345                 350

Asp Ile Thr Trp Thr Leu Cys Gly Thr Pro Asp Tyr Leu Ala Pro Glu
        355                 360                 365

Val Val Gln Ser Lys Gly Tyr Asn Lys Ser Val Asp Trp Tyr Ala Leu
    370                 375                 380

Gly Val Leu Ile Phe Glu Met Leu Ala Gly Tyr Pro Pro Phe Phe Thr
385                 390                 395                 400

Glu Asp Gly Asn Pro Met Lys Leu Tyr Glu Lys Ile Ile Ala Gly Lys
                405                 410                 415

Val Arg Tyr Pro Thr Tyr Phe Asp Val Leu Ala Lys Glu Leu Leu Lys
            420                 425                 430

Asn Leu Leu Ile Gly Asp Leu Thr Lys Arg Tyr Gly Asn Leu Arg Ala
        435                 440                 445

Gly Ser Ser Asp Ile Phe Ala His Gly Trp Phe Ala Glu Val Asp Trp
    450                 455                 460

Asp Lys Leu Tyr Arg Arg Glu Ile Pro Ala Pro Tyr Val Pro Lys Ile
465                 470                 475                 480

Asp Gly Glu Gly Asp Ala Ser Gln Phe Asp Arg Tyr Gln Glu Ala Asp
                485                 490                 495

Val Ser Ala Tyr Gly Lys Val Gly Asn Gly Pro Tyr Asp His Phe Phe
            500                 505                 510

Val Glu Phe
        515

<210> SEQ ID NO 9
<211> LENGTH: 381
<212> TYPE: PRT
<213> ORGANISM: Leishmania sp.

<400> SEQUENCE: 9

Met Leu Val Ser Val Lys Pro Lys Pro Glu Val Ala Gly Thr Ala His
```

```
                 1               5                   10                  15

Val Pro Leu Gly Pro Thr Gly Thr Asn Val Arg Gly Ala Phe Pro Ile
                        20                  25                  30

Thr Ala Ala Ser Arg Ser Ala His Ala Met Phe Pro Ser Thr Trp Tyr
                        35                  40                  45

Ser Ala Leu Lys Pro Lys Val Ala Cys Asn Phe Ala Lys Pro Asp Thr
                50                  55                  60

Ser Ser Trp Lys Leu Ser Asp Phe Glu Leu Lys Asn Thr Leu Gly Thr
        65                  70                  75                  80

Gly Ser Phe Gly Arg Val Arg Ile Ala His Arg Lys Gly Thr Glu Glu
                        85                  90                  95

Tyr Tyr Ala Ile Lys Cys Leu Arg Lys Arg Glu Ile Ile Lys Met Lys
                        100                 105                 110

Gln Gln Gln His Val Ala Gln Glu Lys Gly Ile Leu Met Glu Leu Cys
                        115                 120                 125

His Pro Phe Ile Val Asn Met Met Cys Ser Phe Gln Asp Glu Lys Lys
                        130                 135                 140

Val Tyr Phe Leu Leu Glu Phe Val Met Gly Gly Glu Met Phe Thr His
        145                 150                 155                 160

Leu Arg Thr Ala Gly Arg Phe Pro Asn Asp Val Ala Lys Phe Tyr His
                        165                 170                 175

Ala Glu Leu Val Leu Ala Phe Glu Tyr Leu His Ser Leu Asp Val Ile
                        180                 185                 190

Tyr Arg Asp Leu Lys Pro Glu Asn Leu Leu Asp Asn Lys Gly His
                        195                 200                 205

Val Lys Met Thr Asp Phe Gly Phe Ala Lys Lys Val Pro Asp Arg Thr
        210                 215                 220

Phe Thr Leu Cys Gly Thr Pro Glu Tyr Leu Ala Pro Glu Val Ile Gln
        225                 230                 235                 240

Ser Lys Gly His Gly Lys Ala Val Asp Trp Trp Thr Met Gly Val Leu
                        245                 250                 255

Leu Tyr Glu Phe Ile Ala Gly Tyr Pro Pro Phe Tyr Asp Asp Thr Pro
                        260                 265                 270

Phe Arg Ile Tyr Glu Lys Ile Leu Ala Gly Arg Leu Lys Phe Pro Asn
                        275                 280                 285

Trp Phe Asp Gly Arg Ala Arg Asp Leu Val Lys Gly Leu Leu Gln Thr
                        290                 295                 300

Asp His Thr Lys Arg Leu Gly Thr Leu Lys Gly Gly Pro Ala Asp Val
        305                 310                 315                 320

Lys Asn His Pro Tyr Phe His Gly Ala Asn Trp Asp Lys Leu Tyr Ala
                        325                 330                 335

Arg Tyr Tyr Pro Ala Pro Ile Pro Val Arg Val Lys Ser Pro Gly Asp
                        340                 345                 350

Thr Ser Asn Phe Glu Lys Tyr Pro Asp Ser Pro Val Asp Arg Thr Pro
                        355                 360                 365

Ala Leu Thr Ser Ala Gln Gln Ala Glu Leu Lys Gly Phe
                        370                 375                 380

<210> SEQ ID NO 10
<211> LENGTH: 462
<212> TYPE: PRT
<213> ORGANISM: Amblyomma

<400> SEQUENCE: 10
```

```
Met Asn Ile Phe Lys Asn Arg Gly Arg Lys Lys Glu Lys Gly Pro Val
1               5                   10                  15

Glu Val Val Ala Val Thr Leu Tyr Asp Ala Phe Asp Gly Gln Gln Gln
            20                  25                  30

Gln Gln Ala Pro Gly Gly Pro Lys Ser Ala Ser Ala Pro Ala Thr Pro
        35                  40                  45

Gln Gly Gly Gly Ala Gly Gly His Ala Ala Ser Gln Ser Ser Gln Gln
50                  55                  60

Gln Pro Gln Gln Lys Asp Lys Asp Lys Gln Ser Pro Ala Ala Gly Ala
65                  70                  75                  80

Pro Val Arg Gly Asn Gly Leu Ser Pro Pro Cys Pro Gln Ser Ala Pro
                85                  90                  95

Cys Thr Pro Pro Ala Thr Ser Asn Asn Thr Thr Ala Ser Asn Gln Ala
                100                 105                 110

Thr Thr Ser Ala Asp Met Pro Pro Phe Lys Glu Pro Lys Asp Phe Glu
            115                 120                 125

Arg Phe Leu Glu Glu Ala Arg Lys Ser Phe Glu Gln Lys Trp Thr Ser
        130                 135                 140

Pro Ser Ser Asn Thr Ala Ser Leu Asp Asp Phe Asp Arg Ile Lys Thr
145                 150                 155                 160

Leu Gly Thr Gly Ser Phe Gly Arg Val Met Leu Val Gln His Lys Gln
                165                 170                 175

His Lys Asp Tyr Phe Ala Met Lys Ile Leu Asp Lys Gln Lys Val Val
            180                 185                 190

Lys Leu Lys Gln Val Glu His Thr Leu Asn Glu Lys Arg Ile Leu Gln
        195                 200                 205

Ala Val Glu Phe Pro Phe Leu Val Lys Leu Ala Tyr His Phe Lys Asp
    210                 215                 220

Asn Ser Asn Leu Tyr Met Val Leu Glu Tyr Val Leu Gly Gly Glu Met
225                 230                 235                 240

Phe Ser His Leu Arg Lys Ser Gly Arg Phe Ser Glu Pro His Ala Arg
                245                 250                 255

Phe Tyr Gly Ala Gln Ile Val Leu Ala Phe Gln Tyr Leu His Ser Leu
            260                 265                 270

Asp Leu Ile Tyr Arg Asp Leu Lys Pro Glu Asn Leu Leu Ile Asp His
        275                 280                 285

Thr Gly Tyr Ile Lys Val Thr Asp Phe Gly Phe Ala Lys Arg Val Arg
    290                 295                 300

Gly Arg Thr Trp Thr Leu Cys Gly Thr Pro Glu Tyr Leu Ala Pro Glu
305                 310                 315                 320

Ile Ile Leu Ser Lys Gly Tyr Asn Lys Ala Val Asp Trp Trp Ala Leu
                325                 330                 335

Gly Val Leu Val Tyr Glu Met Ala Ala Gly Tyr Pro Pro Phe Phe Ala
            340                 345                 350

Asp Gln Pro Ile Gln Ile Tyr Glu Lys Ile Val Ser Gly Lys Val Arg
        355                 360                 365

Phe Pro Ser His Phe Thr Ser Asp Leu Lys Asp Leu Leu Arg Asn Leu
    370                 375                 380

Leu Gln Val Asp Leu Thr Lys Arg Phe Gly Asn Leu Lys Asn Gly Val
385                 390                 395                 400

Asn Asp Ile Lys Asn His Arg Trp Phe Ala Thr Thr Asp Trp Ile Ala
                405                 410                 415

Ile Tyr Lys Lys Glu Val Glu Ala Pro Phe Val Pro Lys Cys Lys Gly
```

```
                    420              425              430
Pro Gly Asp Thr Ser Asn Phe Asp Glu Tyr Glu Glu Ala Leu Arg
        435                  440                  445

Ile Ser Ser Thr Glu Lys Cys Ala Arg Glu Phe Ala Glu Phe
        450                  455                  460

<210> SEQ ID NO 11
<211> LENGTH: 353
<212> TYPE: PRT
<213> ORGANISM: Anopheles sp.

<400> SEQUENCE: 11

Met Gly Asn Asn Ala Thr Ser Ala Asn Lys Lys Val Asp Ala Ala Glu
1                5                  10                  15

Ser Val Arg Glu Phe Leu Asp Gln Ala Lys Glu Asp Phe Glu Glu Lys
            20                  25                  30

Trp Lys Arg Asn Pro Thr Asn Thr Ala Ala Leu Asp Asp Phe Glu Arg
        35                  40                  45

Ile Lys Thr Leu Gly Thr Gly Ser Phe Gly Arg Val Met Ile Val Gln
    50                  55                  60

His Lys Ser Thr Lys Asp Tyr Tyr Ala Met Lys Ile Leu Asp Lys Gln
65                  70                  75                  80

Lys Val Val Lys Leu Lys Gln Val Glu His Thr Leu Asn Glu Lys Arg
                85                  90                  95

Ile Leu Gln Ala Ile Ser Phe Pro Phe Leu Val Ser Leu Lys Phe His
            100                 105                 110

Phe Lys Asp Asn Ser Asn Leu Tyr Met Val Leu Glu Tyr Val Pro Gly
        115                 120                 125

Gly Glu Met Phe Ser His Leu Arg Lys Val Gly Arg Phe Ser Glu Pro
    130                 135                 140

His Ser Arg Phe Tyr Ala Ala Gln Ile Val Leu Ala Phe Glu Tyr Leu
145                 150                 155                 160

His Tyr Leu Asp Leu Ile Tyr Arg Asp Leu Lys Pro Glu Asn Leu Leu
                165                 170                 175

Ile Asp Ser Gln Gly Tyr Leu Lys Val Thr Asp Phe Gly Phe Ala Lys
            180                 185                 190

Arg Val Lys Gly Arg Thr Trp Thr Leu Cys Gly Thr Pro Glu Tyr Leu
        195                 200                 205

Ala Pro Glu Ile Ile Leu Ser Lys Gly Tyr Asn Lys Ala Val Asp Trp
    210                 215                 220

Trp Ala Leu Gly Val Leu Val Tyr Glu Met Ala Ala Gly Tyr Pro Pro
225                 230                 235                 240

Phe Phe Ala Asp Gln Pro Ile Gln Ile Tyr Glu Lys Ile Val Ser Gly
                245                 250                 255

Lys Val Arg Phe Pro Ser His Phe Gly Ser Glu Leu Lys Asp Leu Leu
            260                 265                 270

Arg Asn Leu Leu Gln Val Asp Leu Thr Lys Arg Tyr Gly Asn Leu Lys
        275                 280                 285

Ala Gly Val Asn Asp Ile Lys Gly His Arg Trp Phe Ala Ser Thr Asp
    290                 295                 300

Trp Ile Ala Val Phe Gln Lys Arg Ile Glu Ala Pro Phe Ile Pro Arg
305                 310                 315                 320

Cys Lys Gly Pro Gly Asp Thr Ser Asn Phe Asp Asp Tyr Glu Glu Glu
                325                 330                 335
```

Thr Leu Arg Ile Ser Ser Thr Glu Lys Cys Ala Lys Glu Phe Ala Glu
340 345 350

Phe

<210> SEQ ID NO 12
<211> LENGTH: 395
<212> TYPE: PRT
<213> ORGANISM: Danio

<400> SEQUENCE: 12

Met Ala Gln Pro Lys Asp Pro His Phe Gly His Ser Ser Gly Thr Asn
1               5                   10                  15

Ser Ala Leu Gln Lys Leu Asp Thr Leu Ala Ser Arg Phe Phe Tyr Lys
                20                  25                  30

Cys Arg Lys Gly Asn His Asp Lys Gly Leu Glu Asn Gly Pro His
            35                  40                  45

Val Ser Glu His Thr Val Leu Trp Asp Thr Ala Met Lys Glu Thr Leu
    50                  55                  60

Ala Lys Ala Lys Glu Asp Phe Leu Asn Lys Trp Glu Cys Gln Gln Lys
65                  70                  75                  80

Ser Thr Ala Cys Leu Asp Asp Phe Asp Lys Leu Lys Thr Leu Gly Thr
                85                  90                  95

Gly Ser Phe Gly Arg Val Met Leu Val Lys His Lys Gln Ser Glu Gln
            100                 105                 110

Tyr Phe Ala Met Lys Ile Leu Asp Lys Leu Lys Val Val Lys Leu Lys
        115                 120                 125

Gln Ile Glu His Thr Leu Asn Glu Lys Lys Ile Leu Gln Ala Val Ser
    130                 135                 140

Phe Pro Phe Leu Val Lys Leu Glu Cys Ala Phe Lys Asp Asn Ser Asn
145                 150                 155                 160

Leu Tyr Met Val Met Arg Tyr Ile Gln Gly Gly Glu Met Phe Ser His
                165                 170                 175

Leu Arg Arg Ile Gly Arg Phe Ser Glu Gln Asn Ala Arg Phe Tyr Ala
            180                 185                 190

Ala Gln Ile Val Leu Thr Phe Glu Tyr Leu His Met Leu Asp Leu Ile
        195                 200                 205

Tyr Arg Asp Leu Lys Pro Glu Asn Leu Leu Ile Asp His Gln Gly Tyr
    210                 215                 220

Ile Gln Val Thr Asp Phe Gly Phe Ala Lys Arg Val Lys Gly Arg Thr
225                 230                 235                 240

Trp Thr Leu Cys Gly Thr Pro Glu Tyr Leu Ala Pro Glu Ile Ile Leu
                245                 250                 255

Ser Lys Gly Tyr Asn Lys Ala Val Asp Trp Trp Ala Leu Gly Val Leu
            260                 265                 270

Ile Tyr Glu Met Ala Ala Gly Tyr Pro Pro Phe Phe Ala Asp Gln Pro
        275                 280                 285

Ile Gln Ile Tyr Glu Lys Ile Val Ser Gly Lys Val Arg Tyr Pro Ser
    290                 295                 300

His Phe Ser Ser Asp Leu Lys Asp Leu Leu Arg Asn Leu Leu Gln Val
305                 310                 315                 320

Asp Leu Thr Lys Arg Phe Gly Asn Leu Lys Asn Gly Val Ser Asp Ile
                325                 330                 335

Lys Asn His Arg Trp Phe Ala Ser Thr Asp Trp Ile Ala Ile Tyr Glu
            340                 345                 350

```
Lys Lys Val Asp Ala Pro Ile Ile Pro Lys Cys Arg Gly Pro Gly Asp
        355                 360                 365

Thr Ser Asn Phe Asp Glu Tyr Asp Glu Glu Val Ile Arg Val Ser Val
        370                 375                 380

Ser Glu Gln Cys Ser Lys Glu Phe Leu Asp Phe
385                 390                 395

<210> SEQ ID NO 13
<211> LENGTH: 351
<212> TYPE: PRT
<213> ORGANISM: Xenopus sp.

<400> SEQUENCE: 13

Met Gly Asn Ala Ala Thr Ala Lys Lys Gly Asn Glu Ile Glu Ser Val
1               5                   10                  15

Lys Glu Phe Leu Ala Lys Ala Lys Glu Asp Phe Leu Arg Lys Trp Glu
                20                  25                  30

Thr Pro Pro Gln Asn Thr Ala Ser Leu Asp Asp Phe Asp Arg Met Lys
            35                  40                  45

Thr Leu Gly Thr Gly Ser Phe Gly Arg Val Met Leu Val Lys His Lys
        50                  55                  60

Gly Ala Glu Gln Tyr Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Arg Leu Glu Tyr Ser Phe Lys
            100                 105                 110

Asp Asn Ser Asn Leu Tyr Met Ile Met Glu Tyr Val Pro Gly Gly Glu
        115                 120                 125

Met Phe Ser His Leu Arg Arg Ile Gly Arg Phe Ser Glu Pro His Ala
130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Tyr Gly Asn Leu Lys Asn Gly
        275                 280                 285

Val Asn Asp Ile Lys Asn His Lys Trp Phe Ala Thr Thr Asp Trp Ile
290                 295                 300

Ala Ile Tyr Gln Arg Lys Val Glu Ala Pro Phe Ile Pro Lys Cys Arg
305                 310                 315                 320

Gly Pro Gly Asp Thr Ser Asn Phe Asp Asp Tyr Glu Glu Glu Asp Ile
                325                 330                 335
```

Arg Val Ser Leu Thr Glu Lys Cys Ala Lys Glu Phe Ala Asp Phe
            340                 345                 350

<210> SEQ ID NO 14
<211> LENGTH: 351
<212> TYPE: PRT
<213> ORGANISM: Homo sapiens

<400> SEQUENCE: 14

Met Gly Asn Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
            35                  40                  45

Thr Leu Gly Thr Gly Ser Phe Gly Arg Val Met Leu Val Lys His Lys
            50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
            85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
            115                 120                 125

Met Phe Ser His Leu Arg Arg Ile Gly Arg Phe Ser Glu Pro His Ala
            130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
            165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
            195                 200                 205

Glu Ile Ile Leu Ser Lys Gly Tyr Asn Lys Ala Val Asp Trp Trp Ala
            210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
            245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
            275                 280                 285

Val Asn Asp Ile Lys Asn His Lys Trp Phe Ala Thr Thr Asp Trp Ile
            290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
            325                 330                 335

Arg Val Ser Ile Asn Glu Lys Cys Gly Lys Glu Phe Ser Glu Phe
            340                 345                 350

<210> SEQ ID NO 15
<211> LENGTH: 825
<212> TYPE: DNA
<213> ORGANISM: Coronaviridae ORF3a
<220> FEATURE:
<221> NAME/KEY: misc_feature
<222> LOCATION: (31)..(33)
<223> OTHER INFORMATION: n is a, c, g, or t

<400> SEQUENCE: 15

```
atggatttgt ttatgagatt ttttactctt nnntcaatta ctgcacagcc agtaaaaatt     60
gacaatgctt ctcctgcaag tactgttcat gctacagcaa cgataccgct acaagcctca    120
ctccctttcg gatggcttgt tattggcgtt gcatttcttg ctgtttttca gagcgctacc    180
aaaataattg cgctcaataa aagatggcag ctagcccttt ataagggctt ccagttcatt    240
tgcaatttac tgctgctatt tgttaccatc tattcacatc ttttgcttgt cgctgcaggt    300
atggaggcgc aatttttgta cctctatgcc ttgatatatt ttctacaatg catcaacgca    360
tgtagaatta ttatgagatg ttggctttgt tggaagtgca aatccaagaa cccattactt    420
tatgatgcca actactttgt ttgctggcac acacataact atgactactg tataccatat    480
aacagtgtca cagatacaat tgtcgttact gaaggtgacg gcatttcaac accaaaactc    540
aaagaagact accaaattgg tggttattct gaggataggc actcaggtgt taaagactat    600
gtcgttgtac atggctattt caccgaagtt tactaccagc ttgagtctac acaaattact    660
acagacactg gtattgaaaa tgctacattc ttcatcttta acaagcttgt taaagaccca    720
ccgaatgtgc aaatacacac aatcgacggc tcttcaggag ttgctaatcc agcaatggat    780
ccaatttatg atgagccgac gacgactact agcgtgcctt tgtaa                    825
```

<210> SEQ ID NO 16
<211> LENGTH: 465
<212> TYPE: DNA
<213> ORGANISM: Coronaviridae ORF 3b

<400> SEQUENCE: 16

```
atgatgccaa ctactttgtt tgctggcaca cacataacta tgactactgt ataccatata     60
acagtgtcac agatacaatt gtcgttactg aaggtgacgg catttcaaca ccaaaactca    120
aagaagacta ccaaattggt ggttattctg aggataggca ctcaggtgtt aaagactatg    180
tcgttgtaca tggctatttc accgaagttt actaccagct tgagtctaca caaattacta    240
cagacactgg tattgaaaat gctacattct tcatctttaa caagcttgtt aaagacccac    300
cgaatgtgca aatacacaca atcgacggct cttcaggagt tgctaatcca gcaatggatc    360
caatttatga tgagccgacg acgactacta gcgtgccttt gtaagcacaa gaaagtgagt    420
acgaacttat gtactcattc gtttcggaag aaacaggtac gttaa                    465
```

<210> SEQ ID NO 17
<211> LENGTH: 71
<212> TYPE: PRT
<213> ORGANISM: Arabidopsis sp.

<400> SEQUENCE: 17

```
Ile Glu Leu Val Leu Val Glu Ala Arg Asp Leu Val Ala Ala Asp Ile
1               5                   10                  15

Arg Gly Thr Ser Asp Pro Tyr Val Arg Val Gln Tyr Gly Glu Lys Lys
            20                  25                  30

Gln Arg Thr Lys Val Ile Tyr Lys Thr Leu Gln Pro Lys Trp Asn Gln
        35                  40                  45
```

```
Thr Met Glu Phe Pro Asp Asp Gly Ser Ser Leu Glu Leu His Val Lys
        50                  55                  60
Asp Tyr Asn Thr Leu Leu Pro
 65                  70
```

<210> SEQ ID NO 18
<211> LENGTH: 73
<212> TYPE: PRT
<213> ORGANISM: Caenorhabditis elegans

<400> SEQUENCE: 18

```
Ile Thr Leu Thr Val Leu Cys Ala Gly Gly Leu Ile Ala Lys Asp Lys
 1               5                  10                  15
Thr Gly Lys Ser Asp Pro Tyr Val Thr Ala Gln Val Gly Lys Thr Lys
             20                  25                  30
Arg Arg Thr Arg Thr Ile His Gln Glu Leu Asn Pro Val Trp Asn Glu
         35                  40                  45
Lys Phe His Phe Glu Cys His Asn Ser Thr Asp Arg Ile Lys Val Arg
     50                  55                  60
Val Trp Asp Thr Val Lys Ile Leu Ala
 65                  70
```

<210> SEQ ID NO 19
<211> LENGTH: 77
<212> TYPE: PRT
<213> ORGANISM: Danio

<400> SEQUENCE: 19

```
Leu Thr Val Ser Ile Lys Glu Ala Lys Asn Leu Val Pro Met Asp Pro
 1               5                  10                  15
Asn Gly Leu Ser Asp Pro Tyr Val Lys Leu Lys Leu Ile Pro Asp Pro
             20                  25                  30
Lys Ser Glu Ser Lys Gln Lys Thr Lys Thr Ile Lys Cys Cys Leu Asn
         35                  40                  45
Pro Thr Trp Asn Glu Thr Phe Thr Phe Asn Leu Lys Glu Ser Asp Lys
     50                  55                  60
Asp Arg Arg Leu Ser Val Glu Ile Trp Asp Trp Asp Leu
 65                  70                  75
```

<210> SEQ ID NO 20
<211> LENGTH: 80
<212> TYPE: PRT
<213> ORGANISM: Homo sapiens

<400> SEQUENCE: 20

```
Leu His Val Thr Val Arg Asp Ala Lys Asn Leu Ile Pro Met Asp Pro
 1               5                  10                  15
Asn Gly Leu Ser Asp Pro Tyr Val Lys Leu Lys Leu Ile Pro Asp Pro
             20                  25                  30
Lys Asn Glu Ser Lys Gln Lys Thr Lys Thr Ile Arg Ser Thr Leu Asn
         35                  40                  45
Pro Gln Trp Asn Glu Ser Phe Thr Phe Lys Leu Lys Pro Ser Asp Lys
     50                  55                  60
Asp Arg Arg Leu Ser Val Glu Ile Trp Asp Trp Asp Arg Thr Thr Arg
 65                  70                  75                  80
```

<210> SEQ ID NO 21
<211> LENGTH: 77

-continued

```
<212> TYPE: PRT
<213> ORGANISM: Fugu rubripes

<400> SEQUENCE: 21

Leu His Val Thr Val Gly Glu Ala Arg Asn Leu Ile Pro Met Asp Pro
1               5                   10                  15

Asn Gly Leu Ser Asp Pro Tyr Val Lys Leu Lys Ile Thr Pro Asp Pro
            20                  25                  30

Lys Asn Glu Thr Lys Gln Lys Thr Arg Thr Ile Arg Ser Ser Leu Asn
            35                  40                  45

Pro Cys Trp Asn Glu Ser Phe Thr Phe Lys Leu Lys Pro Ser Asp Lys
        50                  55                  60

Asp Arg Arg Leu Ser Val Glu Val Trp Asp Trp Asp Arg
65                  70                  75
```

We claim:

1. A method for screening for a potential anti-SARS antiviral agent, comprising the steps of:
   (a) exposing SARS coronavirus-infected cells to a candidate compound;
   (b) lysing the SARS coronavirus-infected cells;
   (c) incubating virus particles or subtilisin-treated virions with a cAMP-dependent protein kinase substrate; and
   (d) comparing cAMP dependent protein kinase activity to cells not exposed to the candidate compound.

2. The method of claim 1, wherein inhibition of the cAMP-dependent protein kinase activity in the SARS coronavirus-infected cells indicates that the candidate compound has antiviral activity.

3. The method of claim 2, wherein the candidate compound having antiviral activity inhibits SARS-coronavirus infectivity of a cell.

4. The method of claim 1, wherein the virus particles or subtilisin-treated virions are incubated with the cAMP-dependent protein kinase substrate in the presence of an appropriate buffer.

5. The method of claim 1, wherein the cAMP-dependent protein kinase substrate is Kemptide.

6. The method of claim 1, wherein the cAMP dependent protein kinase activity is measured by counting radiolabelled ATP incorporation in the presence of the cAMP-dependent protein kinase substrate.

7. The method of claim 6, wherein the cAMP-dependent protein kinase substrate is Kemptide.

8. The method of claim 6, wherein reduction of the radiolabelled ATP incorporation within the cAMP-dependent protein kinase substrate indicates that the candidate compound has antiviral activity.

9. A method for screening for a potential anti-SARS antiviral agent, comprising the steps of:
   (a) exposing SARS coronavirus-infected cells to a candidate compound;
   (b) lysing the SARS coronavirus-infected cells; and
   (c) comparing interactions between an ORF3a product and an ORF3b product to cells not exposed to the candidate compound.

10. The method of claim 9, wherein decreased or inhibited interaction between the ORF3a product and the ORF3b product indicates that the candidate compound has antiviral activity.

11. The method of claim 9, wherein the interactions are measured using a gel electrophoresis assay.

12. The method of claim 11, wherein interacting products have a higher position on the gel electrophoresis assay than non-interacting products.

13. The method of claim 12, wherein the interacting products indicates that the candidate compound does not inhibit or decrease the interactions between the ORF3a product and the ORF3b product.

14. The method of claim 9, wherein the candidate compound having antiviral activity inhibits SARS-coronavirus infectivity of a cell.

* * * * *

UNITED STATES PATENT AND TRADEMARK OFFICE
CERTIFICATE OF CORRECTION

PATENT NO. : 7,504,205 B2
APPLICATION NO. : 11/132142
DATED : March 17, 2009
INVENTOR(S) : Adam Godzik and Sergey Sikora It is certified that error appears in the above-identified patent and that said Letters Patent is hereby corrected as shown below:

Column 3, line 34 - the word before "compared" should be "SARS-coronavirus";
Column 3, line 43 - the space between the words "corona" and "virus" should be removed;
Column 5, line 13 - the word after "antagonist" should be deleted;
Column 5, line 14 - the word "ligand" should be deleted;
Column 7, line 45 - between the words "ORF3" and "as" a space should be inserted;
Column 8, line 19 - the word "applicants'" should be changed to "applicants";
Column 8, line 29 - the first letter in the word "applicants" should be lower-case;
Column 8, line 41 - the word "know" should be changed to "known";
Column 9, line 25 - after the word "strategy" and before the period a right hand parenthesis should be inserted;
Column 12, line 41 - the space between the words "anti" and "viral" should be removed;
Column 12, line 53 - before the word "multiwell" the phrase "in a" should be deleted;
Column 12, line 64 - the word "is" should be changed to "are";
Column 13, line 8 - before the word "multiwell" the phrase "in a" should be deleted;
Column 13, line 21 - the word "an" should be changed to "a";
Column 14, line 27 - the first letter of the word "applicants'" should be lower-case;
Column 14, line 31 - before the word "whether" the word "a" should be deleted;
Column 14, line 46 - the word "Sample" should be changed to "Samples".

Signed and Sealed this

Twenty-sixth Day of May, 2009

JOHN DOLL
*Acting Director of the United States Patent and Trademark Office*